US008658611B2

(12) United States Patent
Kumon et al.

(10) Patent No.: US 8,658,611 B2
(45) Date of Patent: Feb. 25, 2014

(54) APOPTOSIS-INDUCING AGENT FOR PROSTATE CANCER CELLS

(76) Inventors: Hiromi Kumon, Okayama (JP); Nam-ho Huh, Okayama (JP); Masakiyo Sakaguchi, Okayama (JP); Yasutomo Nasu, Okayama (JP)

( * ) Notice: Subject to any disclaimer, the term of this patent is extended or adjusted under 35 U.S.C. 154(b) by 0 days.

(21) Appl. No.: 13/006,198

(22) Filed: Jan. 13, 2011

(65) Prior Publication Data
US 2011/0166545 A1  Jul. 7, 2011

Related U.S. Application Data

(62) Division of application No. 11/886,338, filed as application No. PCT/JP2006/300411 on Jan. 10, 2006, now abandoned.

(30) Foreign Application Priority Data

Mar. 15, 2005 (JP) .................................. 2005-073807
Mar. 23, 2005 (JP) .................................. 2005-084495

(51) Int. Cl.
*A61K 48/00* (2006.01)

(52) U.S. Cl.
USPC ....................................................... 514/44 R

(58) Field of Classification Search
USPC ....................................................... 514/44 R
See application file for complete search history.

(56) References Cited

U.S. PATENT DOCUMENTS

2003/0069619 A1* 4/2003 Fenn et al. ..................... 607/101

FOREIGN PATENT DOCUMENTS

WO    WO 03/035108 A1    5/2003

OTHER PUBLICATIONS

Goodman & Gilman's The Pharmacological basis of Therapeutics, McGraw-Hill, New York, NY. pp. 77-101).*
Verma & Somia, (Nature 1997, 389: 239-242 ).*
Verma et al (Annu Rev Biochem. 2005, 74:711-38).*
Gautam et al (Am J Respir Med, 2002; 1(1):35-46).*
Baronzio et al (In vivo 23: 143-146, 2009).*
Abarzua, F. et al., Reduced Expression of REIC/Dkk-3 Gene in Prostate Cancer Cell Lines, XXth EAU Congress-Istanbul, Turkey 2005, [on line], Jan. 10, 2005, European Association of Urology, Abstract ID: 3150, [Retrieved on Mar. 23, 2005], Retrieved from the Internet: <URL: http://www.uroweb.org/index.php?structure id=536>, full text.
Hsieh S.Y., et al., "Dickkopf-3/REIC functions as a suppressor gene of tumor growth", Oncogene, 2004, vol. 23, pp. 9183 to 9189.
Abarzua Fernando, et al., "Adenovirus-Mediated Overexpression of REIC/Dkk-3 Selectively Induces Apoptosis in Human Prostate Cancer Cells through Activation of c-Jun-NH2-Kinase", Cancer Research, Nov. 1, 2005, vol. 65:(21), pp. 9617-9622, full test.
Abarzua, F. et al., "Reduced Expressiono f REIC/Dkk-3 Gene in Prostate Cancer Cell Lines", European Urology Supplements, Mar. 2005, vol. 4, Issue 3, p. 223, Abstract No. 882.
Tsuji, Toshiya. et al., "Antiproliferative Activity of REIC/Dkk-3 and Its Significant Down-Regulation in Non-Small-Cell Lung Carcinomas", Biochemical and Biophysical Research Communications, 2001, vol. 29, pp. 257-263.
Kobayashi, Kazuyasu, et al., "Reduced Expression of the REIC/Dkk-3 gene by promoter-hypermethylation in human tumor cells", Gene (2000) vol. 282, pp. 151-158.
Tsuji, Toshiya. et al., "A REIC Gene Shows Down-Regulation in Human Immortalized Cells and Human Tumor-Derived Cell Lines", Biochemical and Biophysical Research Communications (2000), 268, pp. 20-24.
Nozaki, Isao, et al., Reduced expression of REIC/Dkk-3 gene in non-small cell lung cancer, International Journal of Oncology (2001), 19: 117-121.
Kurose, Kyouhei, et al., "Decreased Expression of REIC/Dkk-3 In Human Renal Clear Cell Carcinoma", The Journal of Urology, vol. 171, pp. 1314-1318, Mar. 2004.
Bafico, Anna, et al., "Novel mechanism of Wnt signaling inhibition mediated by Dickkopf-1 interaction with LRP6/Arrow", Nature Cell Biology, Jul. 2001, vol. 3, pp. 683-686.
Hoang, Bang H., et al., "Dickkopf 3 Inhibits Invasion and Motility of Saos-2 Osteosarcoma Cells by Modulating the Wnt-β-Catenin Pathyway", Cancer Research, Apr. 15, 2004, 64, pp. 2734-2739.
Moon, T. Randall, et al., "The Promise and Perils of Wnt Signaling Through β-Catenin", Science, May 31, 2002, vol. 296, pp. 1644-1646.
Rutkowski, D. Thomas, et al., "A trip to the ER: coping with stress", Trends in Cell Biology, Jan. 2004, vol. 14, No. 1, pp. 20-28.
Mori, Kazutoshi, "Frame Switch Splicing and Regulated Intramembrane Proteolysis: Key words to Understand the Unfolded Protein Response", Traffic 2003: 4: 519-528.

* cited by examiner

*Primary Examiner* — Marcia S Noble
*Assistant Examiner* — Magdalene Sgagias
(74) *Attorney, Agent, or Firm* — Fitch, Even, Tabin & Flannery LLP

(57) ABSTRACT

According to the present invention, an apoptosis-inducing agent for prostate cancer comprising REIC/Dkk-3 DNA or an REIC/Dkk-3 protein, and a therapeutic agent for prostate cancer and an agent for inhibiting prostate cancer metastasis that comprise such apoptosis-inducing agent are provided.
An apoptosis-inducing agent for prostate cancer, comprising, as an active ingredient, an REIC/Dkk-3 protein (a) or (b) or REIC/Dkk-3 DNA (c) or (d):
  (a) a protein consisting of the amino acid sequence represented by SEQ ID NO: 2;
  (b) a protein consisting of an amino acid sequence derived from the amino acid sequence represented by SEQ ID NO: 2 by substitution or deletion of 1 or more amino acids;
  (c) DNA consisting of the nucleotide sequence represented by SEQ ID NO: 1; or
  (d) DNA that hybridizes under stringent conditions to DNA consisting of a nucleotide sequence complementary to the nucleotide sequence represented by SEQ ID NO: 1 and encodes a protein having apoptosis activity; and
a therapeutic agent for prostate cancer comprising such apoptosis-inducing agent are provided.

6 Claims, 31 Drawing Sheets

Bar. 20 μm

Bar: 50 μm

Bar: 200 μm

Bar. 200 μm

Bar. 10 μm

Bar. 200 μm

Bar: 200 μm (Day 21)    Transrectal ultrasonography    Enlarged image

Ad-REIC

Ad-LacZ

Bar: 1cm

* P<0.05

* P<0.01

P<0.0001

Bar: 200 μm

Bar: 200 μm

APOPTOSIS-INDUCING AGENT FOR PROSTATE CANCER CELLS

CROSS REFERENCE TO RELATED APPLICATION

This application is a Divisional patent Application of U.S. application Ser. No. 11/886,338, filed Sep. 14, 2007 now abandoned, which is the U.S. National State Patent Application of PCT International Application No. PCT/JP2006/300411 filed Jan. 10, 2006, which designated the U.S. and was not published under PCT Article 21(2) in English, and this application claims the benefit and foreign priority from Japanese Application No. 2005-073807, filed Mar. 15, 2005, and Japanese Application No. 2005-084495, filed Mar. 23, 2005, the complete disclosures of each of the aforesaid applications, including the sequence listing, are incorporated herein by reference.

SEQUENCE LISTING

The instant application contains a Sequence Listing that has been submitted in CRF form, which listing is hereby incorporated by reference in its entirety, and which corresponds to the paper copy.

TECHNICAL FIELD

The present invention relates to apoptosis induction in prostate cancer cells with the use of the REIC/Dkk-3 gene, which is a tumor-inhibiting gene, an apoptosis-inducing agent for prostate cancer cells, which comprises the REIC/Dkk-3 gene or an expression product thereof, and a therapeutic agent for prostate cancer and an agent for inhibiting prostate cancer metastasis, which comprise the apoptosis-inducing agent.

BACKGROUND ART

Selective elimination of cancer cells is an important key issue in treating cancer. During malignant conversion and progression, various genetic changes occur in cells (Vogelstein, B. et al., Trends Genet 9, 138-41 (1993)). Such mutations could be targets of gene therapies for cancer.

Some types of genes exhibit a selective killing effect on cancer cells when overexpressed. Representative examples of such genes include p53 (Chen, P. L. et al., Science 250, 1576-80 (1990); Fujiwara, T. et al., J Natl Cancer Inst 86, 1458-62 (1994); and Nielsen, L. L. et al., Cancer Gene Ther 4, 129-38 (1997)) and mda-7 (Fisher, P. B. et al., Cancer Biol Ther 2, S23-37 (2003)), which have been known as antioncogenes.

Meanwhile, the REIC/Dkk-3 gene has been known as a gene involved in cell immortalization. It has been reported that expression of the gene is inhibited in cancer cells (see WO01/038523, Tsuji, T. et al., BiochemBiophys Res Commun 268, 20-4 (2000), Tsuji, T. et al., BiochemBiophys Res Commun 289, 257-63 (2001), Nozaki, I. et al., Int J Oncol 19, 117-21 (2001) and Kurose, K. et al., J Urol 171, 1314-8 (2004)).

The REIC/Dkk-3 gene is a member of the Dkk family and has been known to interfere with Wnt signal transduction via Wnt receptors (see Bafico, A. et al., Nat Cell Biol 3, 683-6 (2001) and Hoang, B. H. et al., Cancer Res 64, 2734-9 (2004)). The Wnt genes play pleiotropic roles in critical biological contexts, including cell growth, differentiation, malignant transformation, and the like (see Moon, R. T. et al., Science 296, 1644-6 (2002)). Therefore, similarly, Dkk family members (including 4 genes that have been known to exist in humans) are thought to fulfill important functions regarding cell growth, differentiation, and malignant transformation. However, most of their functions have not yet been elucidated.

DISCLOSURE OF THE INVENTION

It is an objective of the present invention to provide an apoptosis-inducing agent for prostate cancer cells, which comprises REIC/Dkk-3 DNA or the REIC/Dkk-3 protein, and a therapeutic agent for prostate cancer and an agent for inhibiting prostate cancer metastasis, which comprise the apoptosis-inducing agent.

The present inventors have conducted intensive studies of the previously reported relationship between the REIC/Dkk-3 gene and cancer cells. It was discovered that the expression level of the REIC/Dkk-3 gene is reduced in human cancer cell lines and cancer tissue. The downregulation of the REIC/Dkk-3 gene was partially caused by promoter hypermethylation. Overexpression of the REIC/Dkk-3 gene with the use of vectors caused growth inhibition in human osteosarcoma cells. These findings indicate that the REIC/Dkk-3 gene could function as an antioncogene and thus that the REIC/Dkk-3 gene could be a new therapeutic target for human cancer.

In addition, the present inventors have found that the expression level of the REIC/Dkk-3 gene is reduced in highly malignant prostate cancer cells. Thus, they have conducted further intensive studies of the use of the REIC/Dkk-3 gene as a therapeutic agent for prostate cancer. Also, the present inventors have found that it is possible to inhibit prostate cancer by causing REIC/Dkk-3 gene expression in prostate cancer cells so as to induce apoptosis in prostate cancer cells. This has led to the completion of the present invention.

Further, the present inventors have examined effects of prostate cancer metastasis inhibition by the REIC/Dkk-3 gene. As a result, they have found that the REIC gene has metastasis-inhibitory activity in mouse orthotopic transplantation models of prostate cancer, in addition to its localized tumor-inhibitory activity.

Furthermore, the present inventors have found that the combined use of the REIC/Dkk-3 gene and hyperthermia results in the improvement in the effects of prostate cancer treatment and prostate cancer metastasis inhibition.

As a result, the present inventors have completed the present invention.

Specifically, the present invention is described as follows.

[1] An apoptosis-inducing agent for prostate cancer, comprising, as an active ingredient, the following REIC/Dkk-3 protein:
  (a) a protein consisting of the amino acid sequence represented by SEQ ID NO: 2; or
  (b) a protein consisting of an amino acid sequence derived from the amino acid sequence represented by SEQ ID NO: 2 by substitution, deletion, or addition of 1 or more amino acids and having apoptosis activity.
[2] A therapeutic agent for prostate cancer, comprising the apoptosis-inducing agent according to [1].
[3] An apoptosis-inducing agent for prostate cancer, comprising, as an active ingredient, the following REIC/Dkk-3 DNA:
  (c) DNA consisting of the nucleotide sequence represented by SEQ ID NO: 1; or
  (d) DNA that hybridizes under stringent conditions to DNA consisting of a nucleotide sequence complementary to the nucleotide sequence represented by SEQ ID NO: 1 and encodes a protein having apoptosis activity.

[4] A therapeutic agent for prostate cancer, comprising the apoptosis-inducing agent according to [3].

[5] An agent for inhibiting prostate cancer metastasis, comprising the apoptosis-inducing agent according to [1].

[6] An agent for inhibiting prostate cancer metastasis, comprising the apoptosis-inducing agent according to [3].

[7] The therapeutic agent for prostate cancer according to [2] or [4], which is used in combination with hyperthermia.

[8] The agent for inhibiting prostate cancer metastasis according to [5] or [6], which is used in combination with hyperthermia.

This description includes part or all of the contents as disclosed in the descriptions of Japanese Patent Application Nos. 2005-73807 and 2005-084495, which are priority documents of the present application.

The patent or application file contains at least one drawing executed in color. Copies of this patent or patent application publication with color drawing(s) will be provided by the Office upon request and payment of the necessary fee.

Figure 1A:
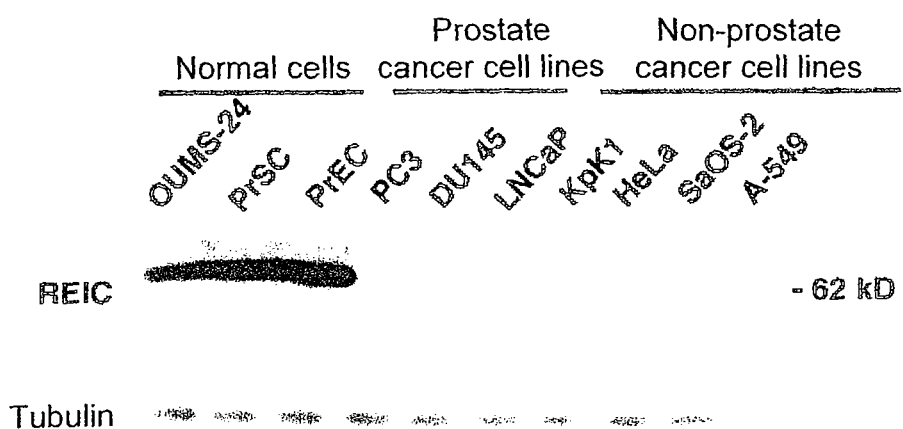
FIG. 1A shows an image of REIC/Dkk-3 expression in normal cells and cancer cells. The image shows REIC protein levels in normal human cells (OUMS-24: normal human fibroblast; PrSC: prostate stromal cell; and PrEC: prostate epithelial cell) and human cancer cell lines (PC3, DU145, and LNCaP: prostate cancer; KpK-1: gastric cancer cell; HeLa: cervical cancer cell; SaOS-2: osteosarcoma; and A-549: squamous carcinoma) obtained by the Western blot method. Tubulin shown in the image was used as a control.
Figure 1B:
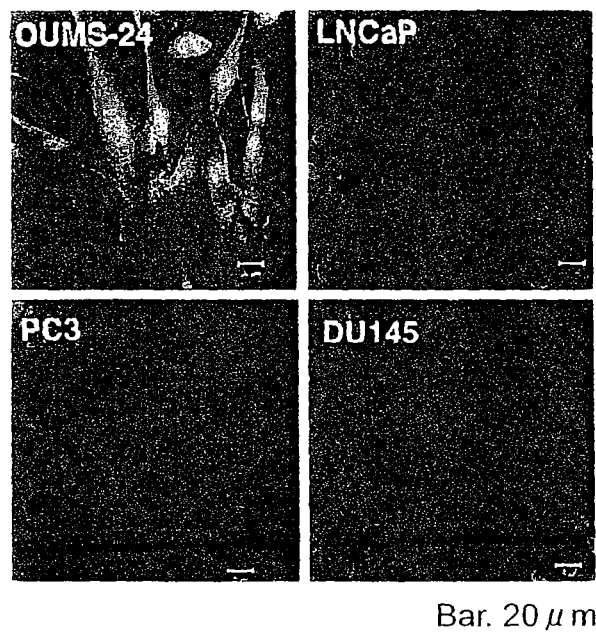

FIG. 1B shows images of REIC/Dkk-3 expression in normal cells and cancer cells. The images show immunostaining results for the REIC/Dkk-3 protein (green) in OUMS-24 and prostate cancer cells (PC3, DU145, and LNCaP). The nuclei were stained with propiodium iodide (red).

Figure 1C:
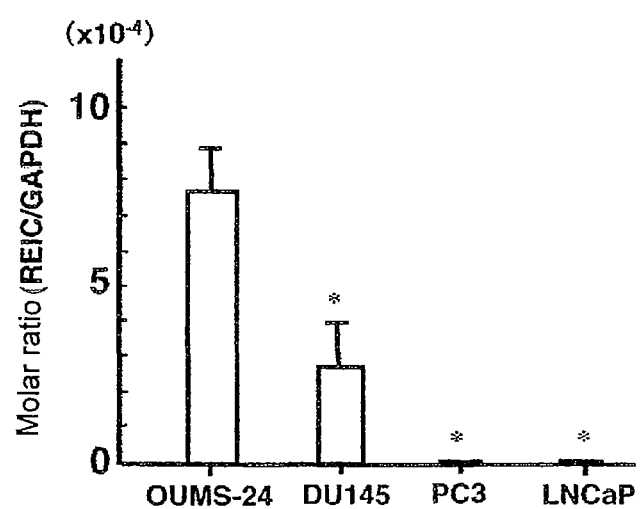

FIG. 1C shows REIC/Dkk-3 expression in normal cells and cancer cells. In the figure, REIC/Dkk-3 mRNA levels of normal human fibroblasts and prostate cancer cell lines, which were analyzed by real-time quantitative RT-PCR, are expressed as molar ratios to those of GAPDH ($p<0.05$).

Figure 1D:
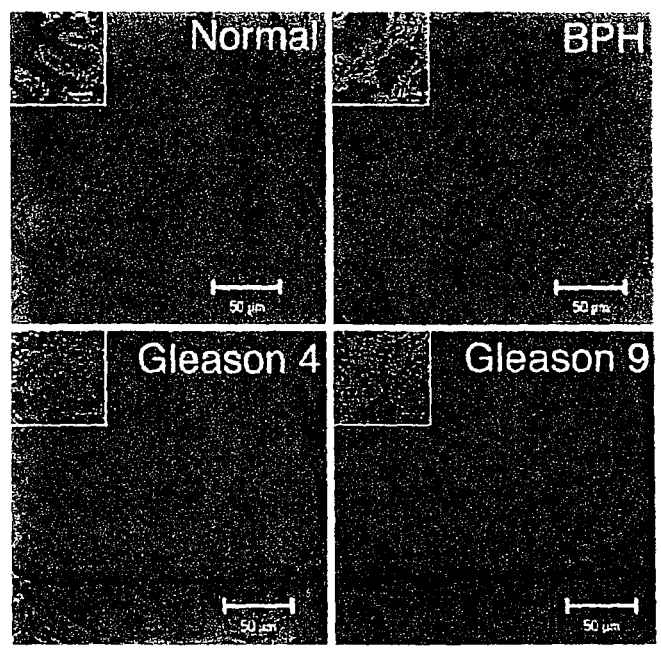

FIG. 1D shows images of the REIC/Dkk-3 expression in normal cells and cancer cells. The images show immunostaining results for REIC/Dkk-3 in a normal prostate, a benign hypertrophic prostate, and prostate cancer tissue sections with Gleason scores of 4 and 9.

Figure 1E:
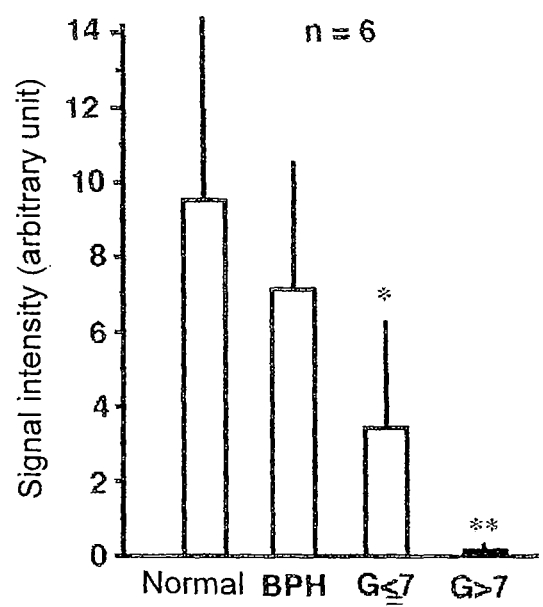

FIG. 1E shows REIC/Dkk-3 expression in normal cells and cancer cells. The figure shows quantitative analysis results for the REIC/Dkk-3 protein using a LandMark tissue Microarray. The abbreviation "BPH" denotes benign hypertrophic prostate tissue and the abbreviation "G" denotes a Gleason score (*$p<0.05$; **$p<0.01$).

Figure 1F:
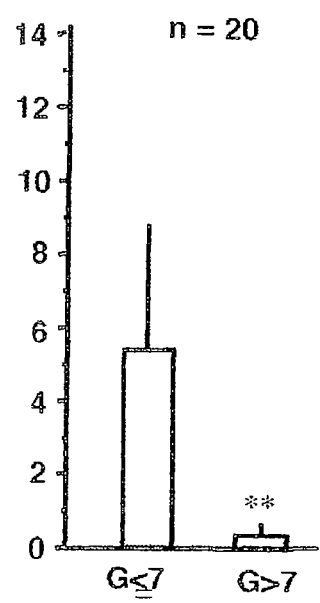

FIG. 1F shows REIC/Dkk-3 expression in normal cells and cancer cells. The figure shows quantitative analysis results for the REIC protein in fresh human prostate cancer tissue sections with Gleason scores of 7 or higher and 7 or lower. The abbreviation "BPH" denotes benign hypertrophic prostate tissue and the abbreviation "G" denotes a Gleason score (*$p<0.05$; **$p<0.01$).

Figure 2A:
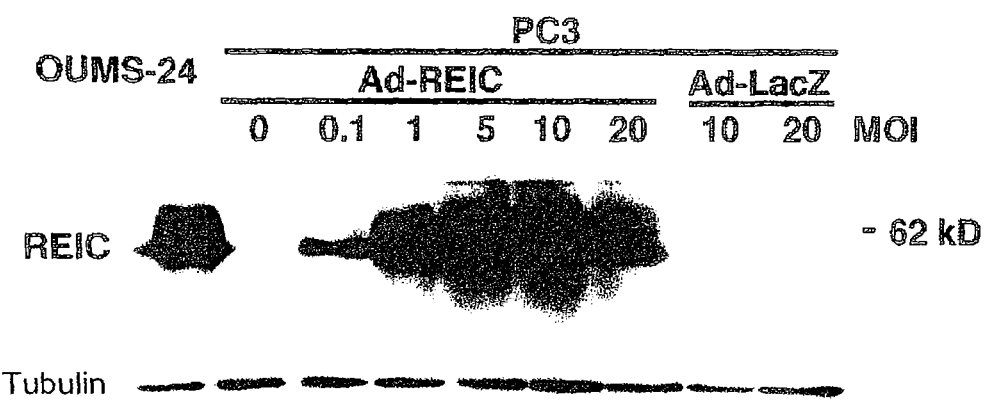

FIG. 2A shows an image of apoptosis induction in human prostate cancer cells caused by REIC/Dkk-3 overexpression. The image shows REIC/Dkk-3 protein expression in prostate cancer cells (PC3) 36 hours after REIC/Dkk-3 cDNA transfection using an adenovirus vector. OUMS-24 was used as a positive control. The abbreviation "Ad-lacZ" denotes an adenovirus vector carrying lacZ.

Figure 2B:
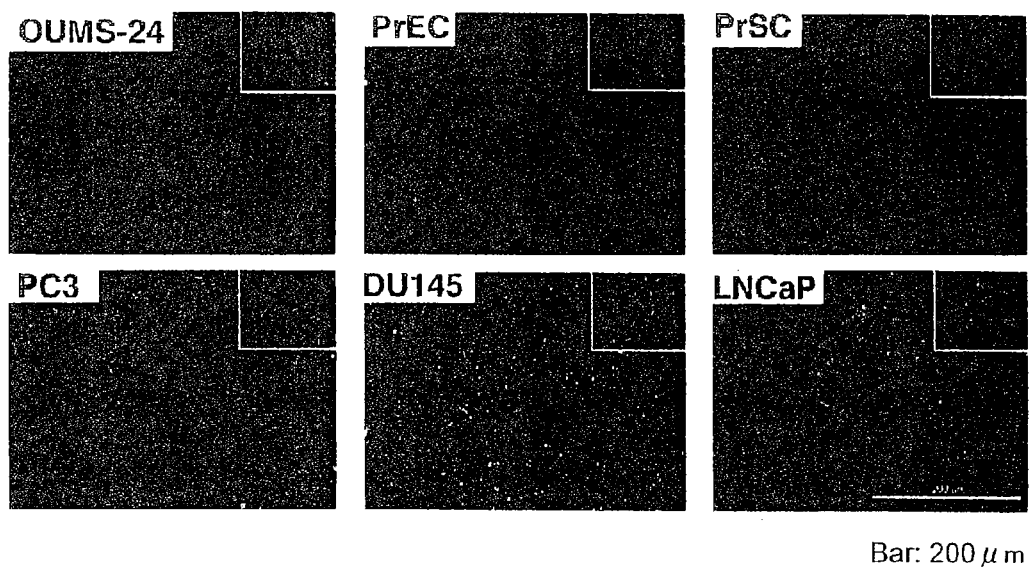

FIG. 2B shows images of apoptosis induction in human prostate cancer cells caused by REIC/Dkk-3 overexpression. The images show TUNEL staining (green) results for normal human prostate cell lines (OUMS-24, PrEC, and PrSC) and prostate cancer cell lines (PC3, DU145, and LNCaP) 36 hours after transfection at 10 MOI. The right upper image shows results of Hoechst 33258 staining (blue).

Figure 2C:
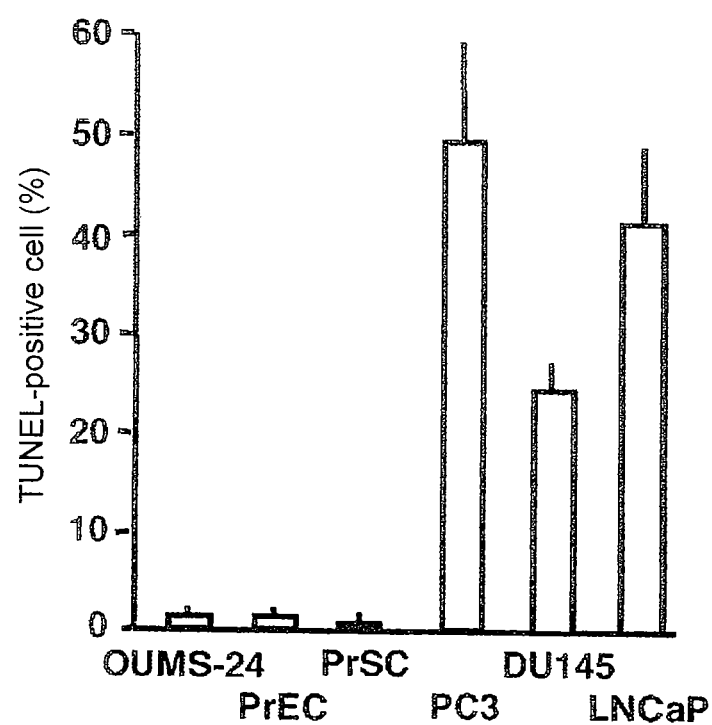

FIG. 2C shows apoptosis induction in human prostate cancer cells caused by REIC/Dkk-3 overexpression. The figure shows percentages of TUNEL-staining-positive cells in normal human prostate cell lines (OUMS-24, PrEC, and PrSC) and those in prostate cancer cell lines (PC3, DU145, and LNCaP) 36 hours after transfection at 10 MOI.

Figure 2D:
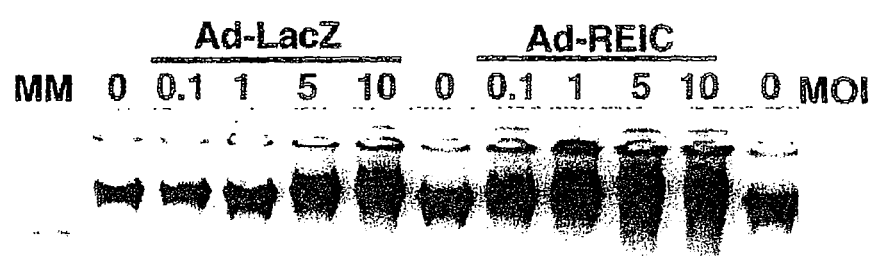

FIG. 2D shows an image of apoptosis induction in human prostate cancer cells caused by REIC/Dkk-3 overexpression. The image shows DNA fragments observed in PC3 cells transfected with Ad-REIC at 1 MOI or higher.

Figure 3A:
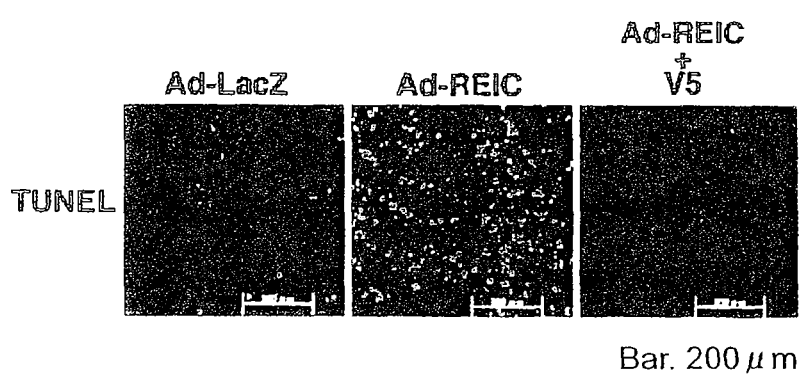

FIG. 3A shows images of the involvement of Bax and JNK in apoptosis induction in PC3 cells caused by Ad-REIC. The images show TUNEL-staining results for PC3 cells 36 hours after transfection with REIC or lacZ at 10 MOI. A peptide inhibitor (V5) for Bax was added at 200 µM to a medium 1 hour prior to transfection. The scale bar corresponds to 200 µm.

Figure 3B:
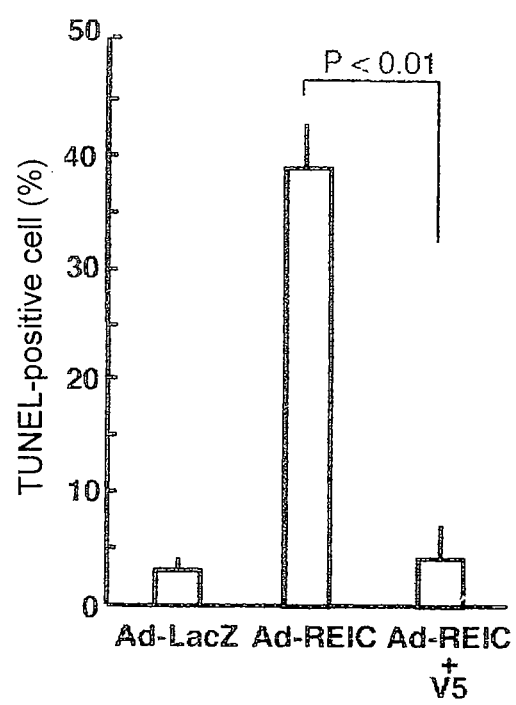

FIG. 3B shows the involvement of Bax and JNK in apoptosis induction in PC3 cells caused by Ad-REIC. The figure shows effects of apoptosis inhibition in PC3 cells caused by a Bax inhibitor V5. The number of TUNEL-positive cells was determined under the same conditions used in 3A.

Figure 3C:
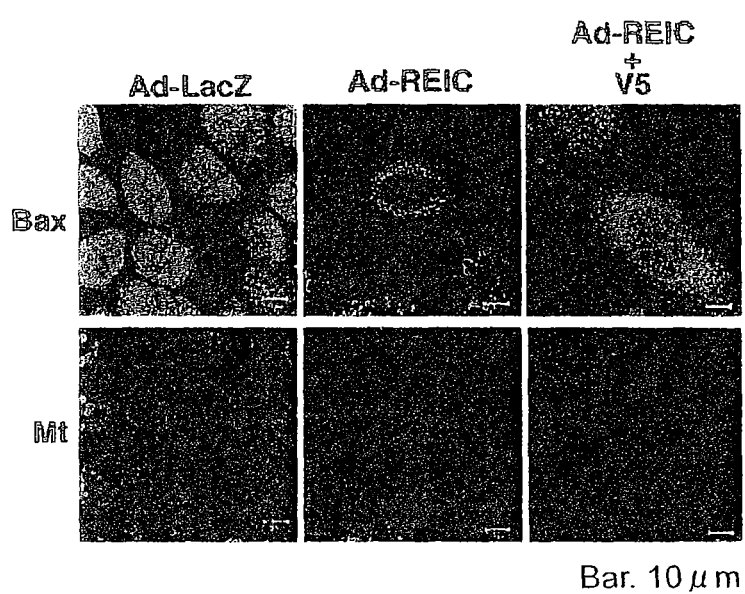

FIG. 3C shows images of the involvement of Bax and JNK in apoptosis induction in PC3 cells caused by Ad-REIC. The images shows immunostaining results for the Bax protein in PC3 cells 36 hours after administration of a vector at 10 MOI. Intracellular localization of mitochondria was visualized by staining using a Mitotracker (Mt).

Figure 3D:
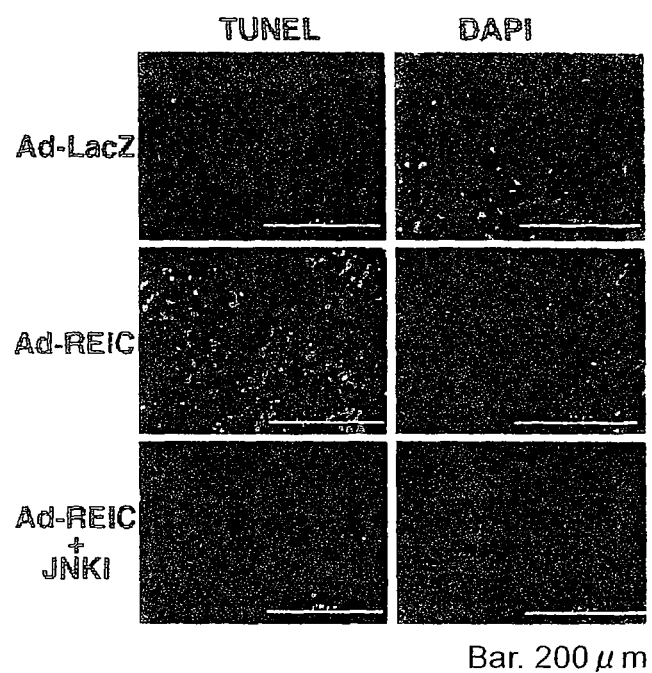

FIG. 3D shows images of the involvement of Bax and JNK in apoptosis induction in PC3 cells caused by Ad-REIC. The images show TUNEL-staining results for PC3 cells treated in the same manner as was used for the examination of FIG. 3A. A JNK inhibitor SP600125 was used at 10 nM.

Figure 3E:
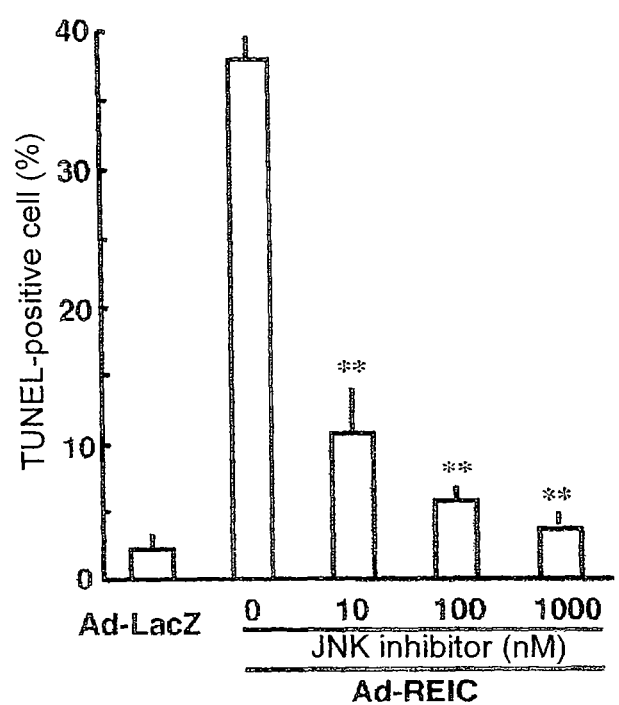

FIG. 3E shows the involvement of Bax and JNK in apoptosis induction in PC3 cells caused by Ad-REIC. The figure shows effects of inhibition of REIC/Dkk-3-induced apoptosis by the INK inhibitor SP600125. The number of TUNEL-positive cells was determined under the same conditions used in 3C.

Figure 3F:
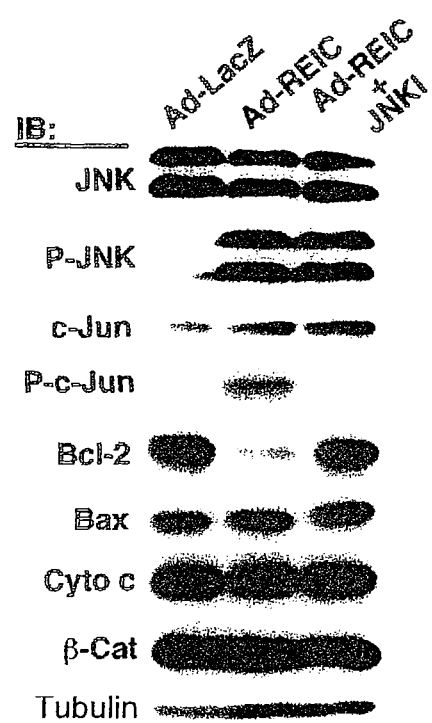

FIG. 3F shows an image of the involvement of Bax and JNK in apoptosis induction in PC3 cells caused by Ad-REIC. The image shows results of Western blot analysis of proteins in PC3 cells as described in 3D. The abbreviation "P" denotes "phosphorylated," the abbreviation "Cyto c" denotes cytochrome c, and the abbreviation "β-cat" denotes β-catenin.

Figure 3G:
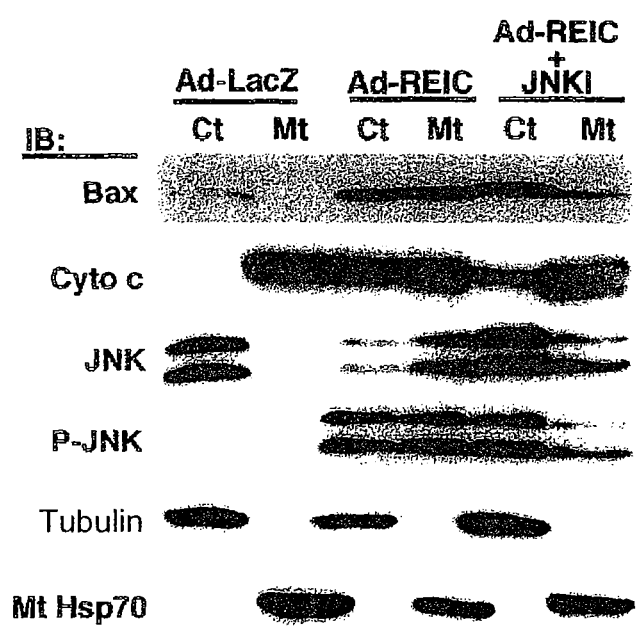

FIG. 3G shows an image of the involvement of Bax and JNK in apoptosis induction in PC3 cells caused by Ad-REIC. The image shows results of Western blot analysis of proteins in cytoplasm and mitochondria extracted from PC3 cells as described in FIG. 3D.

Figure 4A:
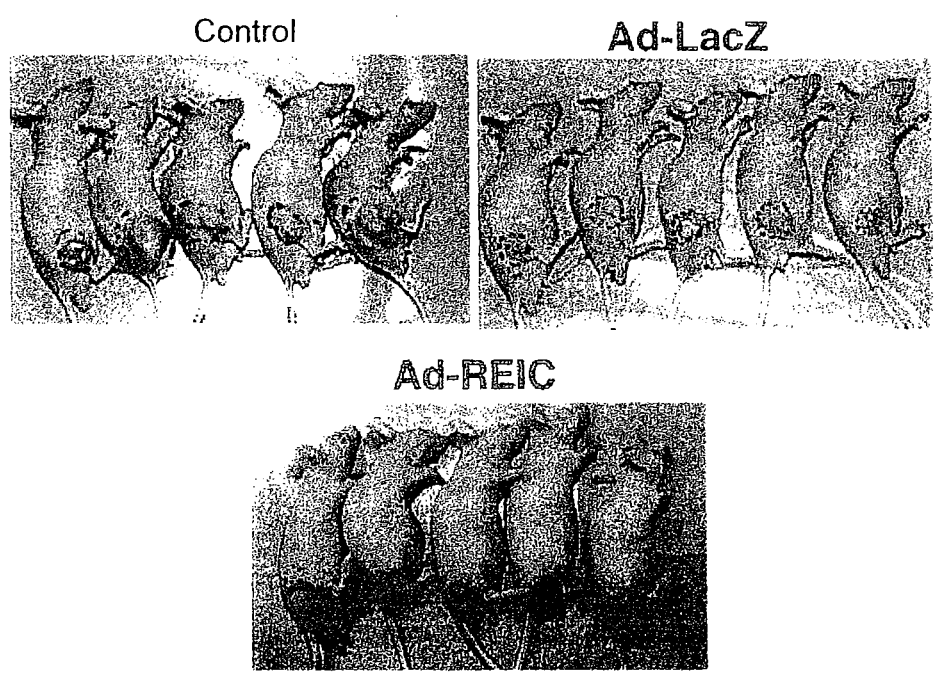

FIG. 4A shows images of effects of Ad-REIC on the growth of PC3 cells in nude mice. The images show appearances of tumors at the end of the observation period.

Figure 4B:
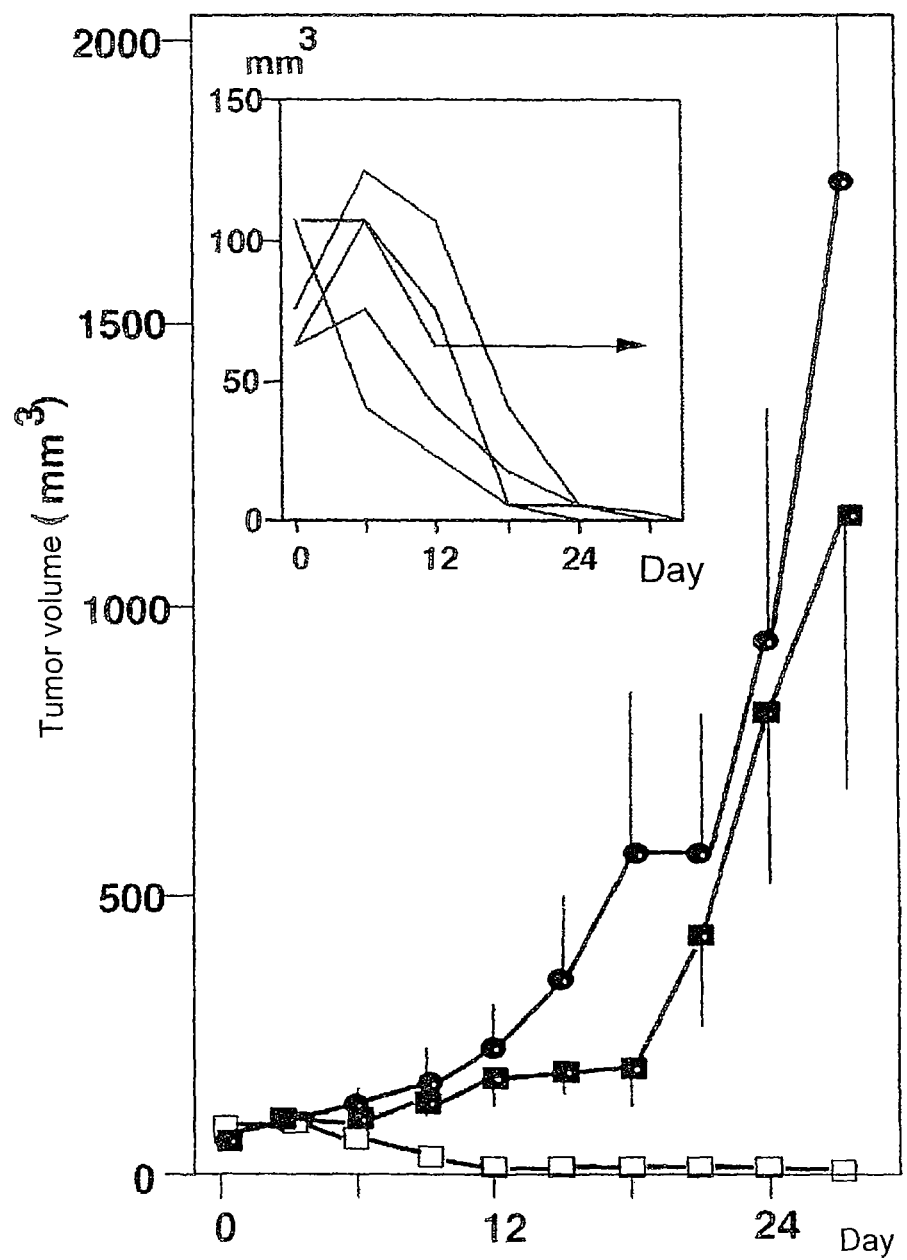

FIG. 4B shows effects of Ad-REIC on the growth of PC3 cells in nude mice. The figure shows the mean volume of tumors of 5 nude mice. The insert figure in FIG. 4B shows tumor volumes for mice subjected to REIC injection. 30 days after virus injection, tumors disappeared in 4 out of 5 mice.

Figure 4C:
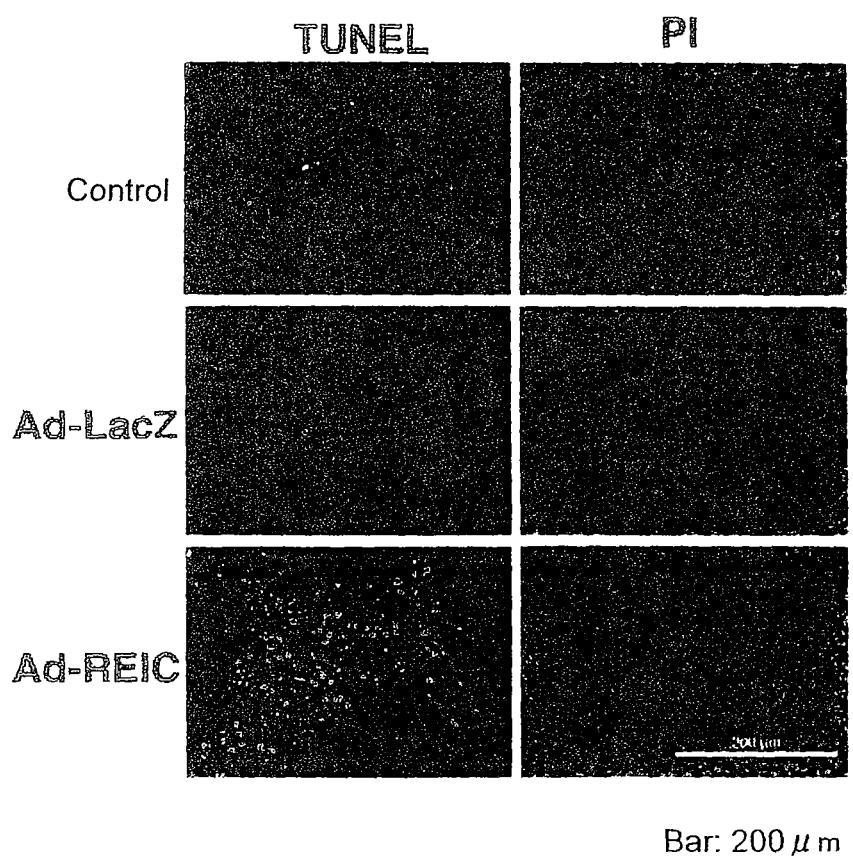

FIG. 4C shows images of effects of Ad-REIC on the growth of PC3 cells in nude mice. The images show TUNEL-staining results for tumor tissue sections 30 days after virus injection. P1 was stained with propiodium iodide for visualization of nuclei.

Figure 5:
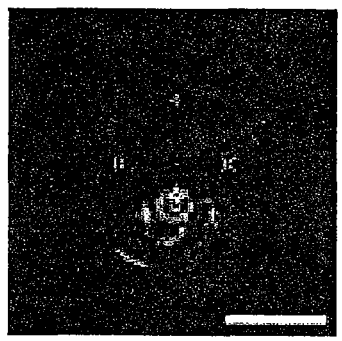
Figure 5:
Figure 5:
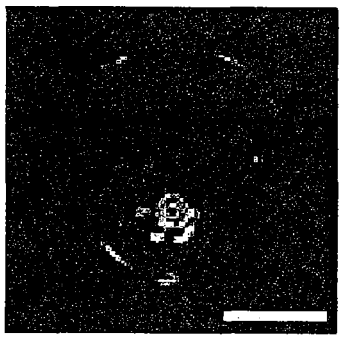
Figure 5:

FIG. 5 shows images of localized tumor-inhibitory activity of the REIC gene in orthotopic transplantation models of prostate cancer.

Figure 6:
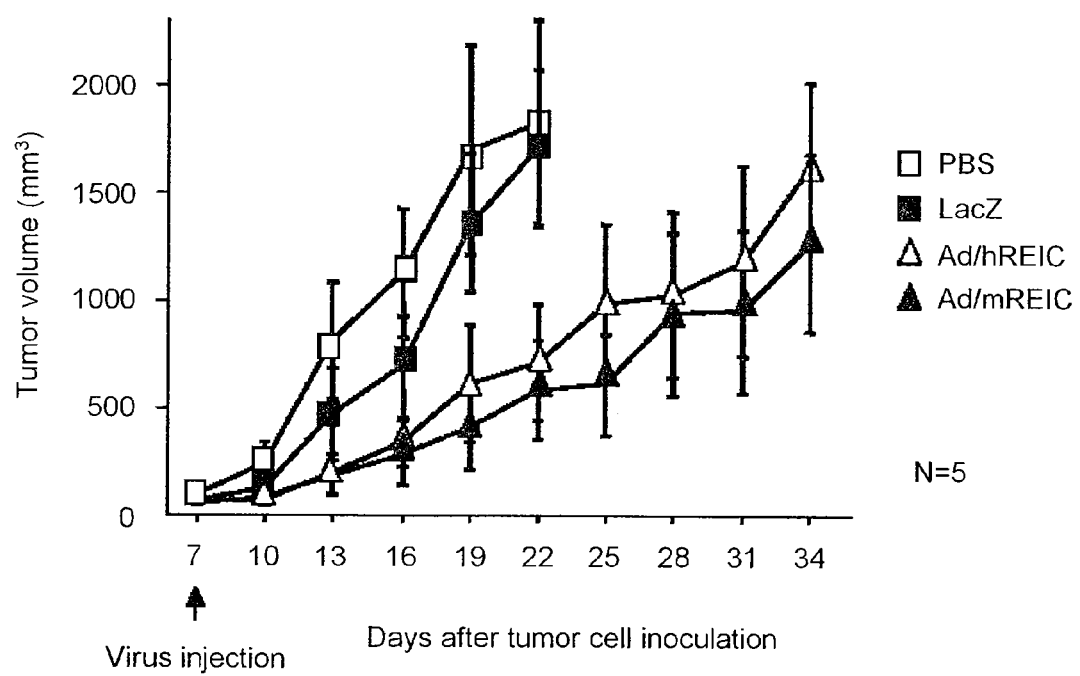

FIG. 6 shows localized tumor-inhibitory activity of the REIC gene in orthotopic transplantation models of prostate cancer.

Figure 7A:
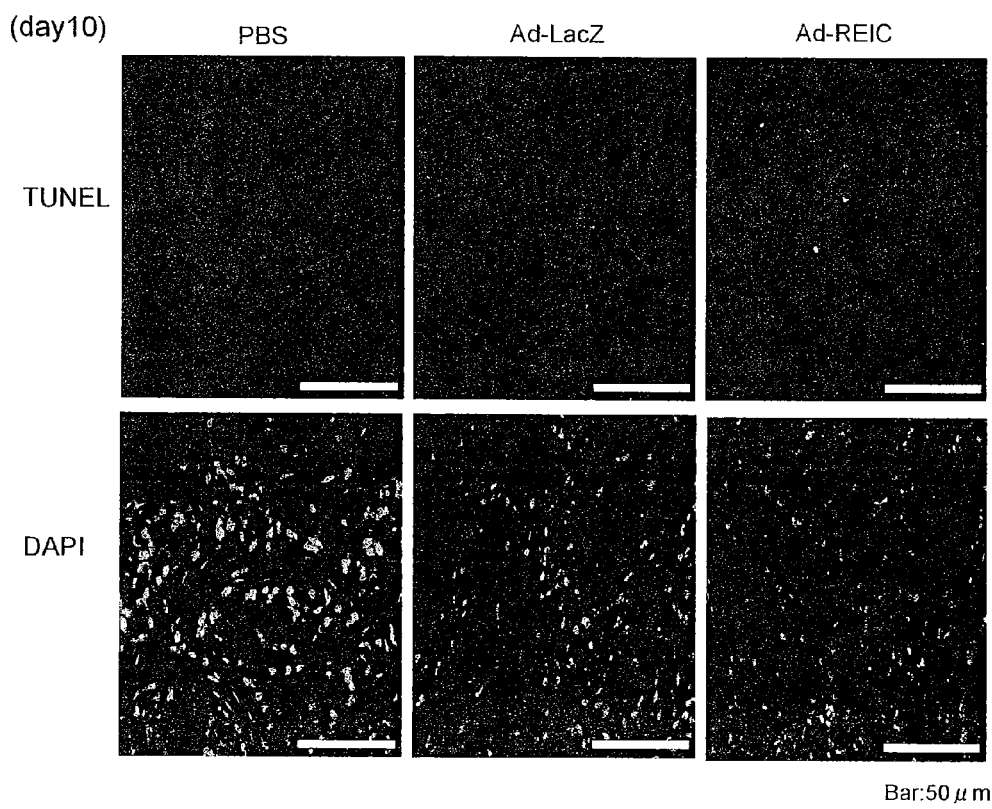

FIG. 7A shows images of apoptosis-inducing effects of the REIC/Dkk-3 gene.

Figure 7B:
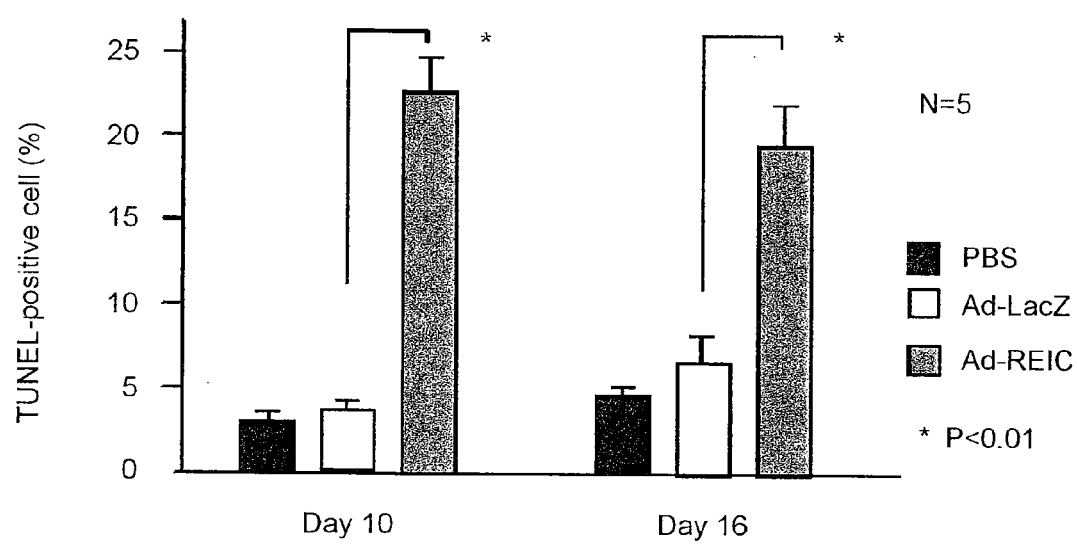

FIG. 7B shows apoptosis-inducing effects of the REIC/Dkk-3 gene.

Figure 8:
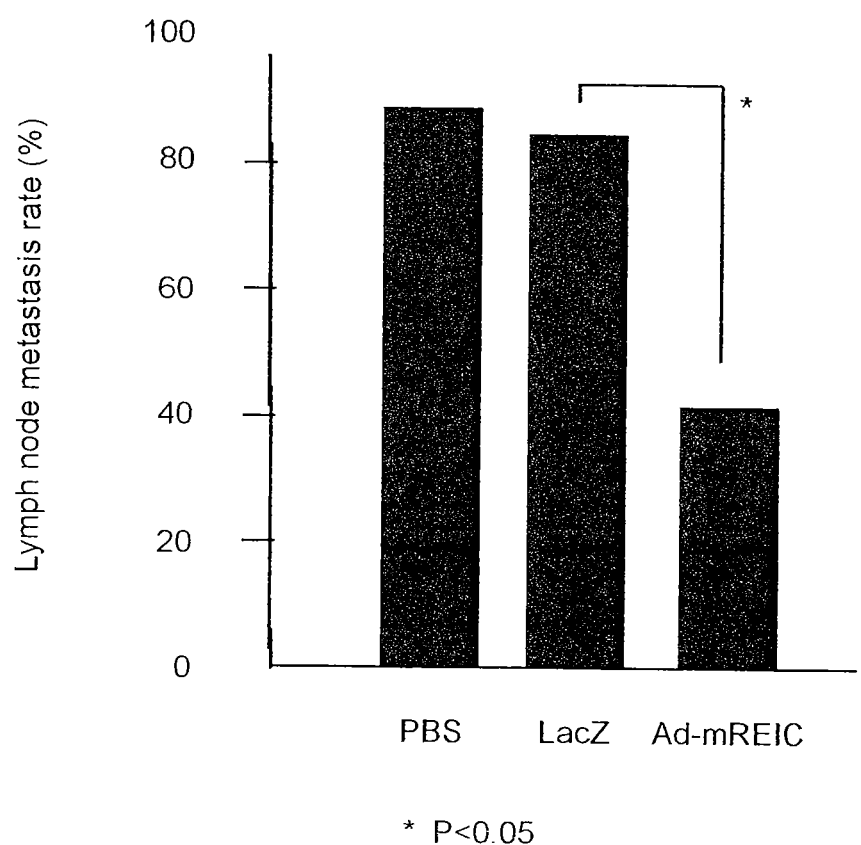

FIG. 8 shows effects of prostate cancer metastasis inhibition by the REIC/Dkk-3 gene as expressed in metastasis rates.

Figure 9:
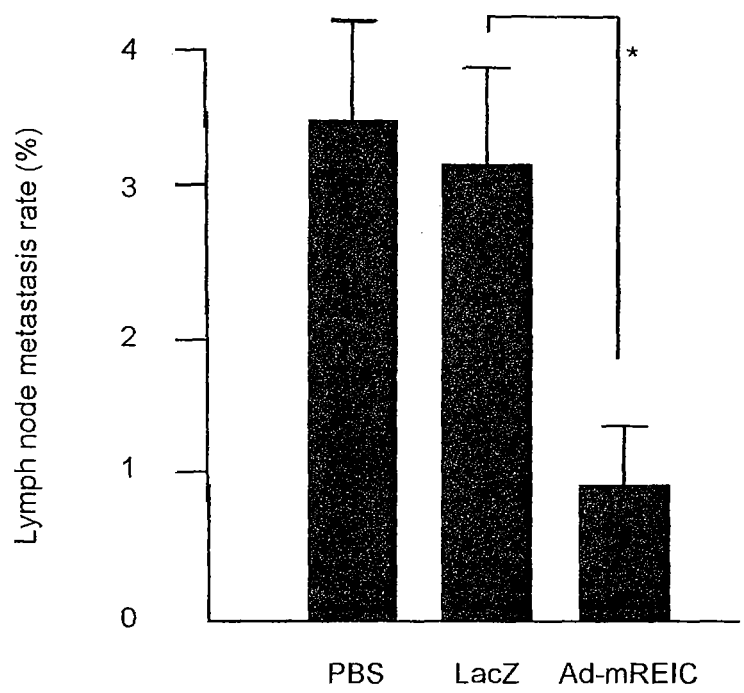

FIG. 9 shows effects of prostate cancer metastasis inhibition by the REIC/Dkk-3 gene as expressed in total numbers of metastatic sites.

Figure 10:
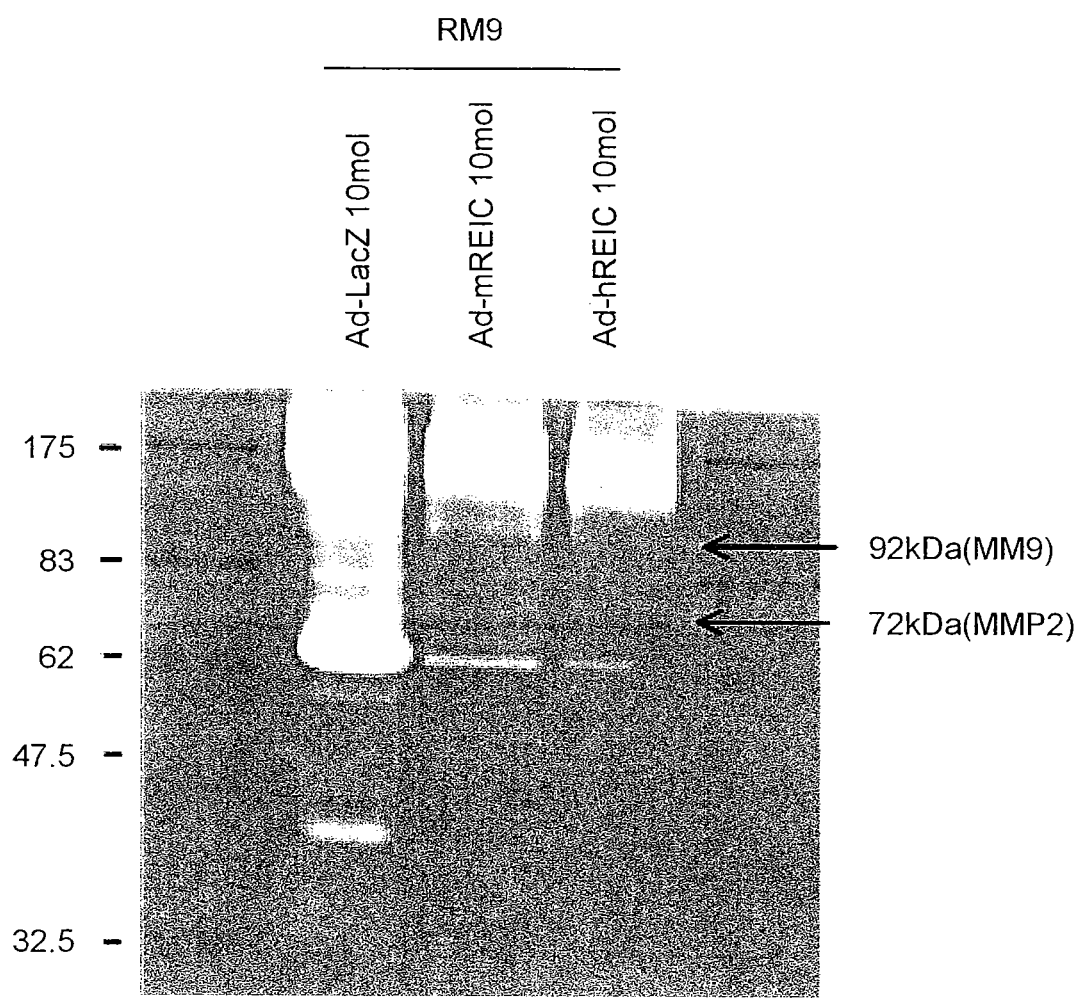

FIG. 10 shows a zymographic image of effects of matrix metalloproteinase activity inhibition by the REIC/Dkk-3 gene.

Figure 11:
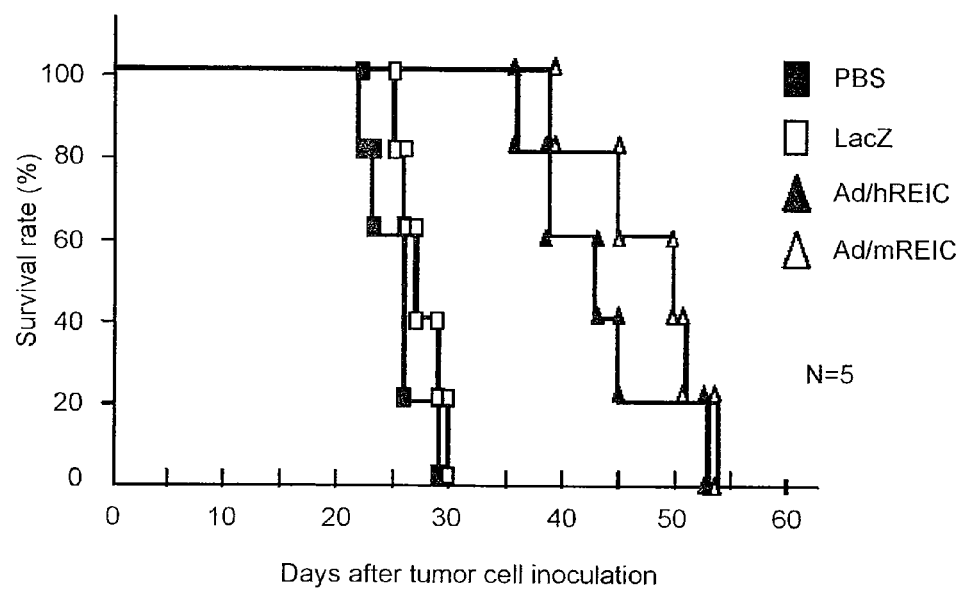

FIG. 11 shows effects of the REIC/Dkk-3 gene upon survival rates of mice inoculated with prostate cancer cells.

Figure 12:
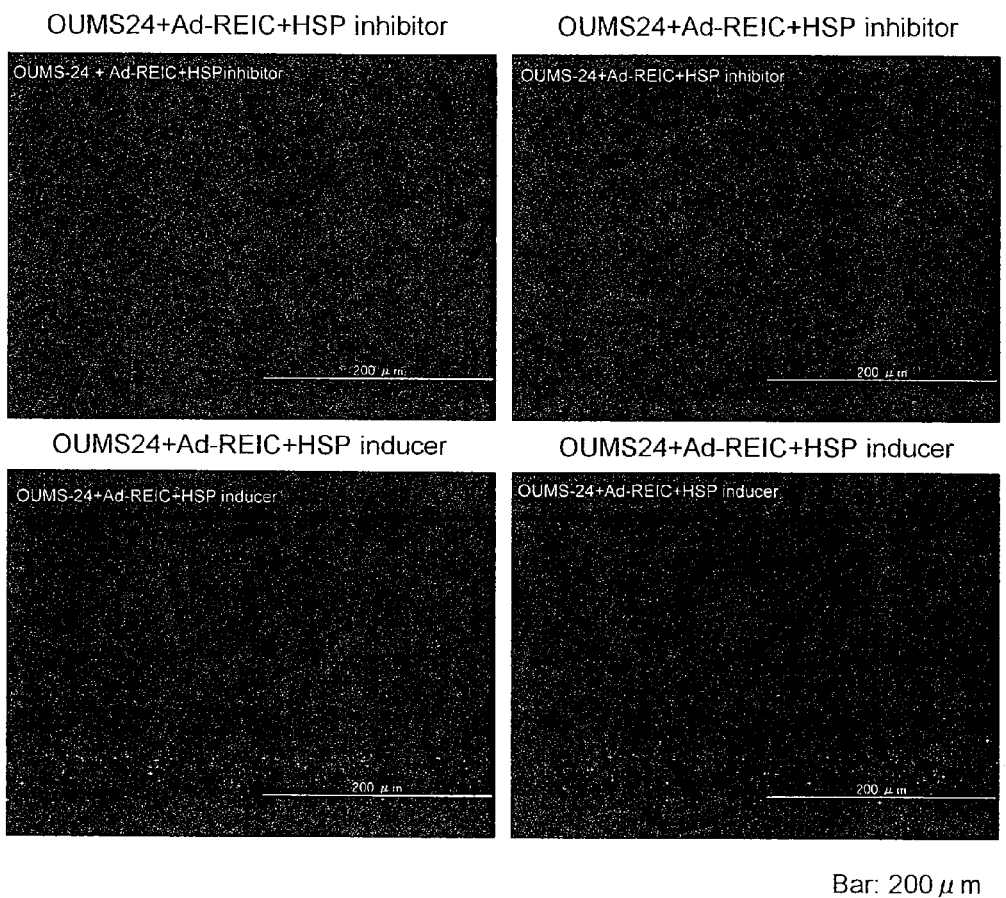

FIG. 12 shows images of apoptosis induction in normal cells caused by the combined use of the REIC/Dkk-3 gene and an HSP inhibitor or an HSP inducer.

Figure 13:
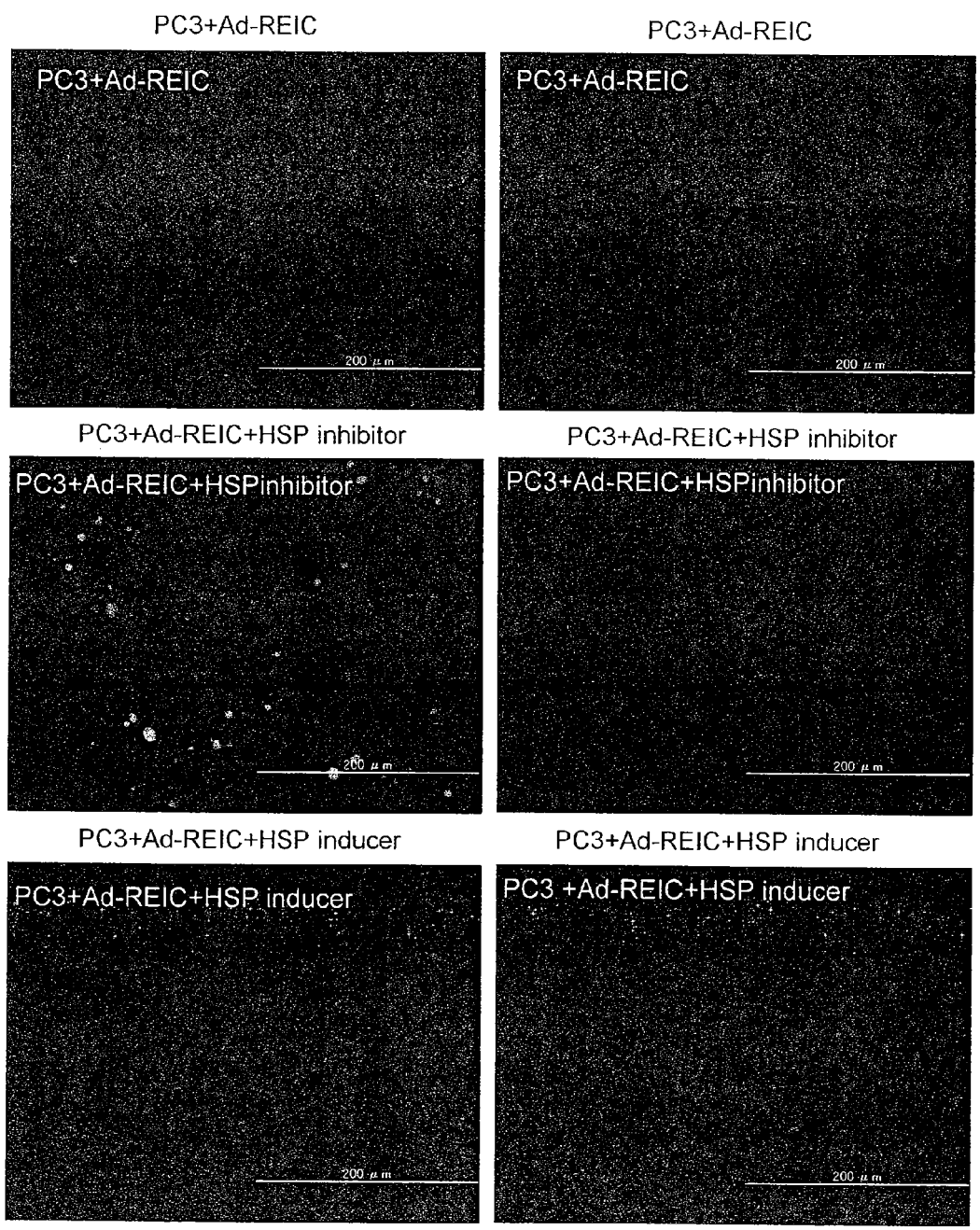

FIG. 13 shows images of apoptosis induction in prostate cancer cells caused by the combined use of the REIC/Dkk-3 gene and an HSP inhibitor or an HSP inducer.

Figure 14:
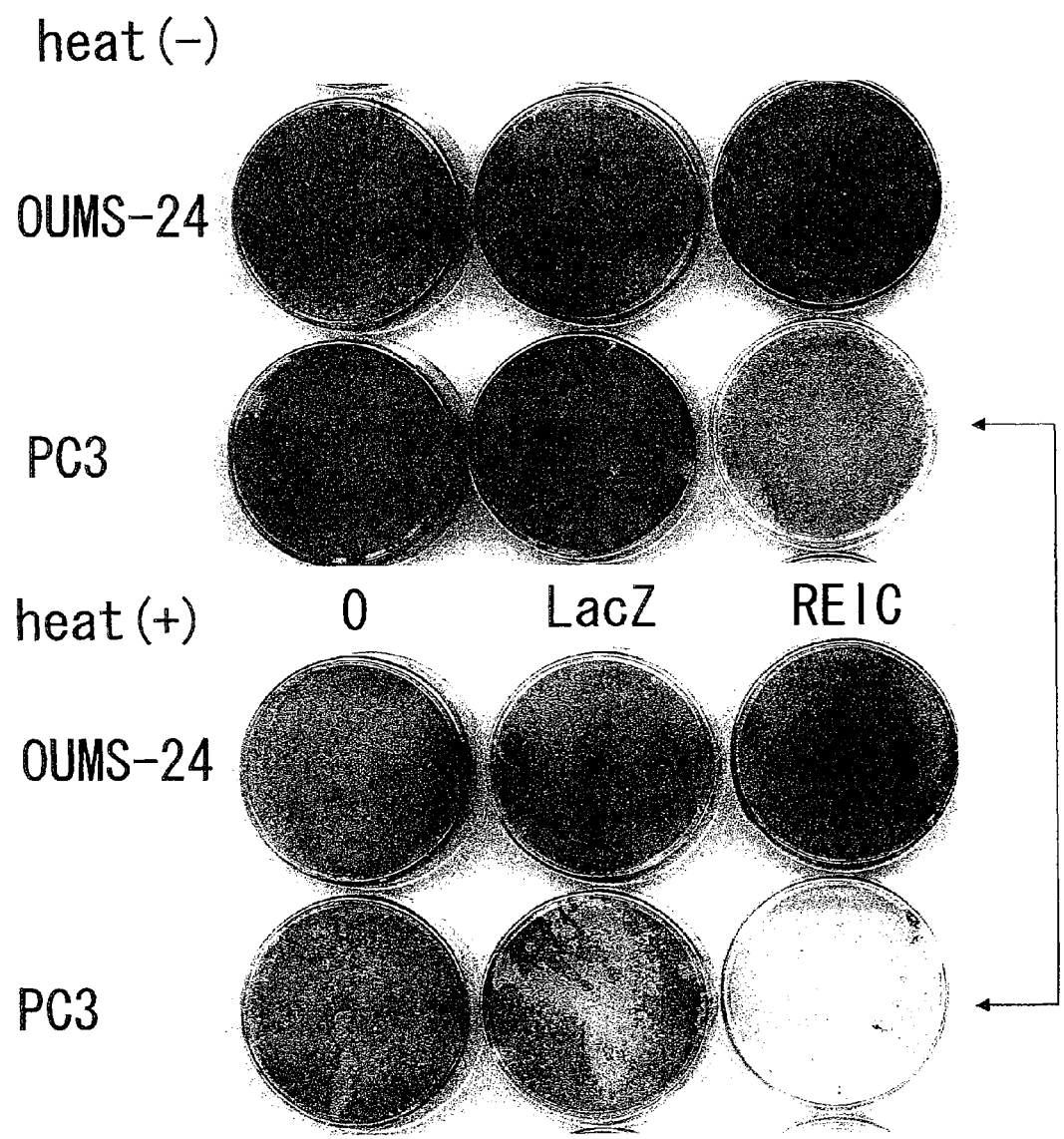

FIG. 14 shows images of effects of the combined use of the REIC/Dkk-3 gene and hyperthermic treatment in prostate cancer cells.

BEST MODE FOR CARRYING OUT THE INVENTION

The apoptosis-inducing agent of the present invention comprises, as an active ingredient, the REIC/Dkk-3 gene or a protein encoded by the gene (REIC/Dkk-3 protein).

The nucleotide sequence of the REIC/Dkk-3 gene and the amino acid sequence of the protein encoded by the gene are represented by SEQ ID NO: 1 and SEQ ID NO: 2, respectively.

As a protein encoded by the REIC/Dkk-3 gene and contained in the apoptosis-inducing agent of the present invention, a protein that has an amino acid sequence that is substantially identical to the amino acid sequence represented by SEQ ID NO: 2 and apoptosis inducing-activity in cancer cells can be used. Herein, examples of such substantially identical amino acid sequence include: an amino acid sequence derived from the amino acid sequence represented by SEQ ID NO: 2 by substitution, deletion and/or addition of 1, several, or more (1 to 10, preferably 1 to 5, and further preferably 1 or 2) amino acids; and an amino acid sequence having a homology of at least 85% or more, preferably 90% or more, further preferably 95% or more, and particularly preferably 97% or more to the aforementioned amino acid sequence upon calculation by BLAST (Basic Local Alignment Search Tool at the National Center for Biological Information, U.S.A.) or the like (with the use of a default (default setting) parameter, for example).

In addition, examples of REIC/Dkk-3 DNA contained in the apoptosis-inducing agent of the present invention include: DNA that hybridizes under stringent conditions to DNA having a nucleotide sequence complementary to the nucleotide sequence represented by SEQ ID NO: 2; DNA having a homology of at least 85% or more, preferably 90% or more, further preferably 95% or more, and particularly preferably 97% or more to the nucleotide sequence represented by SEQ ID NO: 2 upon calculation by BLAST (Basic Local Alignment Search Tool at the National Center for Biological Information, U.S.A.) or the like (with the use of a default (default setting) parameter, for example); and DNA encoding a protein comprising an amino acid sequence derived from the amino acid sequence of a protein encoded by the aforementioned DNA by substitution, deletion and/or addition of 1, several, or more (1 to 10, preferably 1 to 5, and further preferably 1 or 2) amino acids. As long as such DNA encodes a protein having activity of inducing cancer cell apoptosis, it can be contained in the apoptosis-inducing agent of the present invention. The term "stringent conditions" used herein refers to, for example, stringent conditions (1×SSC, 0.1% SDS, 37° C.) or conditions comparable thereto, more stringent conditions (0.5×SSC, 0.1% SDS, 42° C.) or conditions comparable thereto, or even more stringent conditions (0.2×SSC, 0.1% SDS, 65° C.) or conditions comparable thereto. As such hybridization conditions become more stringent, it can be expected that DNA having a high homology to a probe sequence is more likely to be isolated. Note that the above combinations of SSC, SDS, and temperature are mere examples. Thus, a necessary level of stringency can be achieved with the use of an adequate combination of probe concentration, probe length, hybridization reaction time, and the like.

Further, an REIC/Dkk-3 protein and REIC/Dkk-3 DNA, which are contained in the apoptosis-inducing agent, the therapeutic agent for prostate cancer, and the agent for inhibiting prostate cancer metastasis of the present invention, include: a peptide having apoptosis-inducing activity, which is a fragment peptide comprising a partial amino acid sequence of the amino acid sequence of the protein; and a nucleotide encoding a peptide having apoptosis-inducing activity, which is a fragment nucleotide comprising a partial nucleotide sequence of the nucleotide sequence of the DNA, respectively. Such fragment peptide or fragment nucleotide can be readily obtained by cleaving a full-length protein or full-length DNA at an adequate position and detecting the presence or absence of apoptosis-inducing activity in the resulting fragment.

The REIC/Dkk-3 protein of the present invention is administered to a test subject and then incorporated into prostate cancer cells so that the protein acts in the cancer cells and induces apoptosis. The REIC/Dkk-3 protein can be incorporated into prostate cancer cells in a manner such that the REIC/Dkk-3 protein is allowed to bind to, for example, a cell-membrane-permeable peptide such that the protein is administered to a prostate cancer tissue site. A variety of cell-membrane-permeable peptides that have been known to the public can be used. Examples of such peptides include an HIV-1-TAT cell-membrane-permeable domain (protein transduction domain), a cell-membrane-permeable domain of the Drosophila homeobox protein antennapedia, a C-terminal (267-300) peptide of VP22, an HIV-1/Rev (34-50) peptide, an FHV/coat (35-49) peptide, and an N-terminal (7-22) hydrophobic domain of K-FGF. In addition, it is also possible to allow the REIC/Dkk-3 protein to bind to a compound that can specifically bind to cancer cells for administration. In such case, such protein-bound compound may be topically administered to a prostate cancer tissue site or may be administered orally or via other routes, such that the REIC/Dkk-3 protein can be delivered to prostate cancer cells. Examples of such compound that can specifically bind to cancer cells include a homing signal peptide, which is a peptide that binds to a receptor expressed on the cancer cell surface. Examples of such homing signal peptide include NGR and RGD, which specifically bind to a homing signal peptide receptor of an angiogenetic endothelial cell (Nat Med. 1999 September; 5(9): 1032-1038). For instance, in order to allow the above cell-membrane-permeable peptide or homing signal peptide to bind to the REIC/Dkk-3 protein, DNA encoding the REIC/Dkk-3 protein and DNA encoding the above cell-membrane-permeable peptide or homing signal peptide are ligated to each other in-frame such that a fusion protein can be produced by conventional genetic engineering techniques.

The REIC/Dkk-3 gene can be obtained from human cells, human tissue, or the like based on sequence information of SEQ ID NO: 1. In addition, it can be obtained according to WO01/038523.

Further, the present invention encompasses a vector comprising REIC/Dkk-3 DNA. When a test subject is transfected with such vector, the REIC/Dkk-3 protein is expressed in the test subject such that apoptosis-inducing effects can be exerted. Such transfection of a gene of interest into a test subject upon gene therapy can be carried out in accordance with conventional methods. Examples of a method for gene transfection into a test subject include a method using a viral vector and a method using a nonviral vector. A variety of such methods have been known to the public (Experimental Medicine (additional volume), Basic Techniques for Gene Therapy (*Idenshi Chiryo no Kiso Gijutsu*), Yodosha Co., Ltd., 1996; Experimental Medicine (additional volume), Experimental Methods for Gene Transfection & Expression Analysis (*Idenshi Donyu & Hatsugen Kaiseki Jikkenho*), Yodosha Co., Ltd., 1997; "Handbook for Gene Therapy Research and Development" (*Idenshi Chiryo Kaihatsu Kenkyu Handbook*), edited by the Japan Society of Gene Therapy, NTS Inc., 1999).

In typical methods, viral vectors used for gene transfection such as adenovirus, adeno-associated virus, and retrovirus are used. Gene transfection into cells can be carried out by introducing a gene of interest into a DNA or RNA virus such as detoxicated retrovirus, herpesvirus, vaccinia virus, poxvirus, poliovirus, Sindbis virus, Sendai virus, SV40, or human immunodeficiency virus (HIV) and allowing the obtained recombinant virus to infect cells.

When the gene of the present invention is used for a gene therapy using a virus, an adenovirus vector is preferably used. For instance, adenovirus vectors are characterized in that:

(1) gene transfection can be carried out in a variety of cells;

(2) gene transfection can be efficiently performed even in cells in growth arrest;

(3) they can be concentrated by centrifugation such that a virus at high titer (10 to 11 PFU/ml or more) can be obtained; and (4) they are appropriate for use for direct gene transfection into in vivo tissue cells. As an adenovirus vector used for gene therapy, the following vectors have been developed: a second generation adenovirus vector (Lieber, A., et al., J. Virol., 70, 8944, 1996; Mizuguchi, H. & Kay, M. A., Hum. Gene Ther., 10, 2013, 1999) obtained by deleting the E2 or E4 domain in addition to the E1/E3 domain from a first generation adenovirus vector lacking the E1/E3 domain (Miyake, S., et al., Proc. Natl. Acad. Sci. U.S.A., 93, 1320, 1996); and a third generation adenovirus vector (Steinwaerder, D. S. et al., J. Virol., 73, 9303, 1999) almost completely lacking the adenovirus genome (GUTLESS). However, for transfection of the gene of the present invention, any adenovirus vector may be used without particular limitation. Further, the gene of the present invention can be applied for long-term gene expression using, for example, an adeno-AAV hybrid vector having the ability to cause incorporation in the AAV chromosome (Recchia, A. et al., Proc. Natl. Acad. Sci. U.S.A., 96, 2615, 1999) and an adenovirus vector that has acquired the ability to cause incorporation in the chromosome with the use of a transposon gene. In addition, by inserting a peptide sequence that can be translocated to an H1 loop of an adenovirus fiber in a tissue-specific manner, it is possible to impart tissue specificity to an adenovirus vector (Mizuguchi, H. & Hayakawa, T., Nippon Rinsho, 7, 1544, 2000).

Further, even without the use of the above viruses, it is possible to transfect cells or tissue with a gene of interest with the use of a recombinant expression vector comprising a gene expression vector, such as a plasmid vector. For instance, gene transfection into cells can be performed by a lipofection method, a calcium phosphate coprecipitation method, a DEAE-dextran method, and a DNA direct injection method using a micro glass tube. Furthermore, it is possible to allow a recombinant expression vector to be incorporated into cells by a gene transfection method using internal liposomes, a gene transfection method using electorostatic type liposomes, an HVJ-liposome method, a modified HVJ-liposome method (HVJ-AVE liposome method), a method using an HVJ-E (envelope) vector, a method of introducing a receptor-mediated gene, a method of transferring DNA molecules into cells with carriers (metallic particles) using a particle gun, a method of direct transfection of naked DNA, a transfection method using a variety of polymers, or the like. The expression vector used in such case may be any expression vector as long as it can cause in vivo expression of a gene of interest. Examples thereof include expression vectors such as pCAGGS (Gene 108, 193-200 (1991)), pBK-CMV, pcDNA3.1, pZeoSV (Invitrogen Corporation, Stratagene), and pVAX1.

A vector comprising REIC/Dkk-3 DNA may adequately comprise a promoter or enhancer for gene transcription, a polyA signal, a marker gene used for labeling and/or selection of cells transfected with a gene, or the like. In such case, examples of a promoter that can be used include conventional promoters.

In order to introduce a pharmaceutical composition comprising REIC/Dkk-3 DNA of the present invention into a test subject, the following methods or the like may be used: an in vivo method, wherein a gene therapeutic agent is directly introduced into a living body; and an ex vivo method, wherein a specific cell is collected from a human, a gene therapeutic agent is introduced ex vivo into the cell, and the cell is introduced into the human (Nikkei Science, 1994, 4, pp. 20-45; The Pharmaceuticals Monthly, 36(1), 23-48 (1994); Experimental Medicine (additional volume), 12(15), (1994); "Handbook for Gene Therapy Research and Development" (*Idenshi Chiryo Kaihatsu Kenkyu Handbook*), edited by the Japan Society of Gene Therapy, NTS Inc., 1999).

Prostate cancer is a therapeutic target of the present invention. In particular, the present invention is especially useful for highly malignant prostate cancer. The term "highly malignant prostate cancer" used herein indicates, for example, prostate cancer with a Gleason score of 8 or higher.

The REIC/Dkk-3 protein or REIC/Dkk-3 DNA of the present invention can be further used for inhibition of prostate cancer metastasis. That is, the present invention encompasses an agent for inhibiting prostate cancer metastasis comprising, as an active ingredient, the REIC/Dkk-3 protein or REIC/Dkk-3 DNA. The agent for inhibiting prostate cancer metastasis can be used in the same manner as an apoptosis-inducing agent for prostate cancer and a therapeutic agent for prostate cancer. When administering such agent to prostate cancer cells, it is possible to inhibit prostate cancer metastasis.

Further, the REIC/Dkk-3 protein or REIC/Dkk-3 DNA can enhance effects of hyperthermia for prostate cancer. Hyperthermia is a cancer therapy utilizing the cancer cell characteristic of being more heat-sensitive than normal cells. Apoptosis induction by the REIC/Dkk-3 protein is associated with the expression of heat shock protein (HSP) in cells and is affected by cell stress responsiveness. That is, with the combined use of hyperthermia and an apoptosis-inducing agent, cancer therapeutic agent, or agent for inhibiting cancer metastasis that comprises, as an active ingredient, an REIC/Dkk-3 protein or REIC/Dkk-3 DNA, apoptosis is more likely to be induced so that it becomes possible to treat cancer and to inhibit cancer metastasis more effectively. Specifically, upon hyperthermic treatment of cancer regions, the apoptosis-inducing agent, cancer therapeutic agent, or agent for inhibiting cancer metastasis, which comprises, as an active ingredient, the REIC/Dkk-3 protein or REIC/Dkk-3 DNA of the present invention can be administered to the relevant regions. Any heating method may be used for a hyperthermic treatment for hyperthermia as long as it allows a prostate cancer region of a test subject to be subjected to hyperthermic treatment. Either a localized heating method or a whole-body heating method can be adopted. A heating apparatus to be used may be based on any heating method such as an external heating method, an intracavitary heating method, or a tissue heating method. A specific example of a heating apparatus is a heating apparatus equipped with a thermostatic bath and using microwaves, ultrasonic waves, electromagnetic waves, RF waves (radiofrequency waves), or the like. The temperature for hyperthermic treatment is 41° C. to 45° C. and preferably 43° C. to 44° C.

The apoptosis-inducing agent, cancer therapeutic agent, or agent for inhibiting cancer metastasis, which comprises, as an active ingredient, an REIC/Dkk-3 protein or REIC/Dkk-3 DNA of the present invention may be administered prior to, during, or after hyperthermia.

That is, the present invention encompasses a method of treating prostate cancer or inhibiting prostate cancer metastasis, comprising administering an apoptosis-inducing agent, cancer therapeutic agent, or agent for inhibiting cancer metastasis, which comprises, as an active ingredient, an REIC/Dkk-3 protein or REIC/Dkk-3 DNA to a test subject upon hyperthermic treatment of a prostate cancer region of the test subject. Further, the present invention encompasses: an apoptosis-inducing agent, cancer therapeutic agent, or agent for inhibiting cancer metastasis, which comprises, as an active ingredient, an REIC/Dkk-3 protein or REIC/Dkk-3 DNA to be used in combination with hyperthermia; and an apoptosis-inducing agent, cancer therapeutic agent, or agent for inhibiting cancer metastasis, which comprises, as an active ingredient, an REIC/Dkk-3 protein or REIC/Dkk-3 DNA, and which is administered prior to, during, or after application of hyperthermia.

The pharmaceutical composition of the present invention contains an REIC/Dkk-3 protein, a fusion protein comprising the REIC/Dkk-3 protein and a cell-membrane-permeable peptide or a homing signal peptide, REIC/Dkk-3 DNA, or a vector comprising the DNA, together with a pharmaceutically acceptable carrier, diluent, and/or excipient.

The pharmaceutical composition of the present invention can be administered in various forms. For instance, it can be formed into tablets, capsules, granules, powder, syrups, or the like for oral administration. Alternatively, it can be formed into injections, infusions, suppositories, sprays, eye drops, nasal preparations, adhesive preparations, or the like for parenteral administration.

The pharmaceutical composition of the present invention may be topically administered. For instance, the effects thereof can be exerted when the composition is administered to cancer regions by, for example, injection.

The pharmaceutical composition of the present invention contains a carrier, a diluent, and/or an excipient, which are usually used in the pharmaceutical field. Examples of a carrier and an excipient used for tablets include lactose and magnesium stearate. Examples of aqueous liquid used for injection include physiological saline and isotonic solutions containing glucose or different adjuvants, which may be used in combination with adequate solubilizers, including alcohol, polyalcohol such as propylene glycol, and nonionic surfactants. Examples of oily liquid that can be used include sesame oil and soybean oil. Examples of a solubilizer that may be used in combination include benzyl benzoate and benzyl alcohol.

The dose of the pharmaceutical composition of the present invention is determined depending upon patient's symptoms, age, and weight, and the like. Upon oral administration, the daily dose in terms of an REIC/Dkk-3 protein is approximately 0.001 mg to 100 mg. It may be administered in a single dose or multiple doses. In addition, upon parenteral administration, it is possible to carry out subcutaneous, intramuscular, or intravenous administration at 0.001 mg to 100 mg in a single dose. In addition, REIC/Dkk-3 DNA that is inserted into an expression vector or the like so as to be translated in a test subject may be subcutaneously, intramuscularly, or intravenously administered at 0.001 mg to 100 mg in a single dose every several days, weeks, or months.

EXAMPLES

The present invention is hereafter described in greater detail with reference to the following examples, although the technical scope of the present invention is not limited thereto.

Example 1

Prostate Cancer Cell Apoptosis Induction by REIC/Dkk-3

Materials used in the Examples of the present invention were obtained as described below. The Examples were carried out by methods described below.

Cells and Culture Method

Normal prostate epithelial cells (PrEC) and prostate stromal cells (PrSC) were purchased from Cambrex (Baltimore, Md.). The prostate cancer cell lines PC3, DU145, and LNCaP were provided by ATCC (Rockville, Md.). OUMS-24 was provided by Dr. Masayoshi Nanba. An HAM'S F-12 K medium, an RPMI 1640 medium, and modified MEM medium (Nissui) were separately used with a supplement of 10% calf serum for PC3, DU145 and LNCaP, and OUMS-24.

Human Prostate Tissue

A LandMark™ low-density prostate tissue microarray (Ambion, Austin) was used for immunostaining of the REIC/Dkk-3 gene. Fresh prostate cancer tissue samples were obtained from 40 patients. Of them, 20 samples had a Gleason score of 8 or higher and another 20 samples had a Gleason score of 7 or lower.

Immunological Analyses

After fixation with 4% paraformaldehyde, the cells and the tissue samples were immunostained with a primary antibody (anti-human REIC/Dkk-3 antibody purified in the laboratory of the present inventors) and a secondary antibody (FITC-conjugated anti-rabbit immunoglobulin G antibody, Sigma, St. Louis). For Bax and Bcl-2, an anti-human Bax antibody (Upstate Cell signaling solutions, Lake Placid, N.Y.) and an anti-human Bcl-2 antibody (BD Biosciences, San Diego) were used, respectively. A Vectashield mounting medium with DAPI or with propiodium iodide (Vector Laboratories, Burlingame, Calif.) was used for staining of cell nuclei. The signal intensity of each stained sample was quantitated using computer software. Western blot analysis was performed as previously described. The antibodies used were as follows: a purified rabbit anti-human REIC/Dkk-3 antibody; an Apoptosis sampler I kit (BD Biosciences) for Apf-1, Bad, Bcl-2, Bcl-xL, and p53; a rabbit anti-human Bax antibody (Upstate Cell signaling solutions, Lake Placid, N.Y.); a rabbit anti-human Bax antibody (BD Biosciences); a mouse anti-human Apaf-1 antibody (BD Biosciences); and a mouse anti-human tubulin antibody (Sigma).

Real-Time Quantitative RT-PCR

Real-time PCR was performed under the conditions recommended by the manufacturer using a LightCycler™ (Roche Diagnostic, Lewes, UK). The primers used for real-time PCR were as follows:

```
                                        (SEQ ID NO: 3)
REIC/Dkk-3-F 5'-GTAAGTTCCCCTCTGGCTTG-3';

(SEQ ID NO: 4)
REIC/Dkk-3-R 5'-AAGCACCAGACTGTGAAGCCT-3';

(SEQ ID NO: 5)
GAPDH-F 5'-GGGTGTGAACCATGAGAAGTATGA-3';
and (SEQ ID NO: 6)
GAPDH-R 5'-TGCTAAGCAGTTGGTGGTGC-3'.
```

The obtained products were checked by melting point analysis, electrophoresis, and direct sequencing. Standard curves were created using the plasmids containing the respective inserts. The results are shown as molar ratios of REIC/Dkk-3 to GAPDH.

Apoptosis Analyses

A DNA ladder method was performed under conventional conditions. DNA was extracted after lysing cells with Triton X-100, treated with RNase and proteinase K, and electrophoresed on 2% agarose gel. An In Situ Cell Death Detection Kit, Fluorescein (Roche) was used for TUNEL staining. A Bax-specific peptide inhibitor V5 was purchased from Sigma Genosis (Woodlands, Tex.).

Animal Experiments

PC3 cells ($2.5 \times 10^6$/PBS 50 μl) were subcutaneously injected into the right flanks of 8-week-old BALB/C nude mice. One week later, when the tumor diameters had reached 5 mm, adenovirus vectors ($2.5 \times 10^8$ pfu) incorporating the REIC gene (or LacZ gene) were injected intratumorally. The same volume of PBS was injected for controls. Tumor sizes were measured every 3 days up to 30 days after adenovirus vector injection. Tumor volumes (V) were calculated using the following formula: ½×(the shorter diameter)²×(the longer diameter).

In this Example, results described below were obtained.

In order to find the potential usefulness of the REIC/Dkk-3 gene as a therapeutic target, a variety of cells were first examined in terms of REIC/Dkk-3 gene expression. In human fibroblasts (OUMS-24), prostate epithelial cells (PrEC), and prostate stromal cells (PrSC), the REIC/Dkk-3 protein was detected in two bands of 62 to 83 kDa (FIG. 1A). The observed size was larger than the size estimated from the amino acid sequence (38.3 kDa) because of glycosylation.

The REIC/Dkk-3 protein was barely detected in cancer cell lines, excluding 3 representative prostate cancer cell lines (PC3, LNCaP, and DU145) and 4 prostate cancer cell lines. Lack of REIC/Dkk-3 protein in the 3 different prostate cancer cell lines was confirmed by immunostaining (FIG. 1B). Downregulation of REIC/Dkk-3 mRNA was also confirmed by Quantitative RT-PCR (FIG. 1C).

The expression of the REIC/Dkk-3 gene was examined in human prostate tissue by immunostaining (FIG. 1D). The REIC/Dkk-3 protein was detected in epithelial cells and stromal cells in normal prostates and benign hypertrophic prostates. In prostate cancer with a Gleason score of 7 or lower, the REIC/Dkk-3 protein level was reduced differently. In prostate cancer with a Gleason score of 8 to 10, the expression of REIC/Dkk-3 protein was not observed. Signal intensity was quantitatively measured using computer software (FIG. 1E). In both a commercially available prostate tissue microarray (FIG. 1E, left) and fresh prostate cancer tissue (FIG. 1E, right), the expression level of REIC/Dkk-3 protein was reduced in proportion to the cancer grade. Upon immunostaining of other normal human tissues (from the brain, heart, liver, pancreas, kidney, mammary glands, and lymph nodes), the REIC/Dkk-3 protein was expressed at different intensities.

In order to examine the possible use of the REIC/Dkk-3 gene as a gene therapy tool, the REIC/Dkk-3 gene was overexpressed using an adenovirus vector incorporating the REIC/Dkk-3 gene. The REIC/Dkk-3 protein level in PC3 cells transfected with REIC/Dkk-3 with the use of vectors at 1 MOI was almost comparable to that of OUMS-24 (FIG. 2A). Within a few days after transfection, most of the prostate cancer cells had become detached from the bottom of the culture vessel. In order to examine the cause, cells were stained 36 hours after REIC/Dkk-3 gene transfection by the TUNEL method. As shown in FIG. 2B, many prostate cancer cells (PC3, DU145, and LNCaP) were TUNEL-positive while fewer normal cells (OUMS-24, prostate stromal cells, and prostate epithelial cells) were TUNEL-positive. The incidences of TUNEL-positive cells were 49%, 24%, and 41% in the cases of PC3, DU145, and LNCaP, respectively. However, the incidence of TUNEL-positive cells was less than 1% in the case of normal cells (FIG. 2C). DNAs of PC3 cells were analyzed 36 hours after vector transfection so as to confirm apoptotic properties.

In the case of PC3 cells transfected with the REIC gene at 1 MOI or higher, different patterns of DNA bands were clearly observed (FIG. 2D). As shown in FIG. 2D, specific DNA fragments were observed in PC3 cells transfected with Ad-REIC at 1 MOI or higher. One day after seeding of $5 \times 10^5$ PC3 cells, viral vectors were allowed to transfect the cells. The cells were harvested 36 hours after transfection. The transfection efficiency of Ad-REIC and the expression level of the REIC/Dkk-3 gene were similar among the cells (data not shown). These results indicate that overexpression of REIC/Dkk-3 selectively induces apoptosis in prostate cancer cells that substantially lack endogenous REIC/Dkk-3 expression.

In order to discover the mechanism for tumor-specific apoptosis caused by the REIC/Dkk-3 gene, expression levels of different apoptosis/cell-cycle-regulation-related proteins in PC3 cells and OUMS-24 cells were compared. In PC3 cells transfected with the RE1C/Dkk-3 gene, reduced levels of apoptosis-inhibiting Bcl-2 and Bcl-XL proteins were observed (FIG. 3F). No significant changes in levels of Bax, Bad, ApaF-1, p53, p21 (CIP1/WAF1), or p16 (INK4a) were observed among cells (data not shown).

A caspase 8 inhibitor did not inhibit Ad-REIC-induced apoptosis in PC3 cells. Meanwhile, a Bax inhibitor V5 (Sawada, M. et al., Nat Cell Biol 5, 352-7 (2003)) completely inhibited apoptosis (FIG. 3A). Translocation of Bax protein from cytoplasm to mitochondria may trigger activation of a Bax-mediated apoptotic pathway (Gross, A. et al., Embo J 17, 3878-85 (1998)). FIG. 3C shows mitochondrial translocation of Bax protein by Ad-REIC and inhibition of such translocation by V5. V5 showed no effects on the protein levels of Bcl-2 and Bax.

It has been known that c-jun N-terminal kinase (JNK) mediates a non-canonical pathway of Wnt signaling (Lei, K. et al., Mol Cell Biol 22, 4929-42 (2002); and Tsuruta, F. et al., Embo J 23, 1889-99 (2004)). Further, it has been reported that Bax plays an important role in JNK-induced apoptosis and JNK promotes mitochondrial translocation of Bax. When a JNK-specific inhibitor SP600125 was added to PC3 cells, Ad-REIC-induced apoptosis was inhibited in a concentration-dependent manner (FIGS. 3D and 3E). Activation of JNK in PC3 cells infected with Ad-REIC was confirmed using a phosphorylated JNK antibody (FIG. 3F). SP600125 inhibited JNK kinase activity but not phosphorylation of JNK itself. Bax was detected in cytoplasm of PC3 cells but clearly observed to be translocated to mitochondria in Ad-REIC-infected cells (FIG. 3G). The mitochondrial translocation of Bax was associated with the release of cytochrome c into cytoplasm and was suppressed by a JNK inhibitor SP600125. Phosphorylated JNK was also translocated by Ad-REIC to mitochondria. These results suggest that overexpression of REIC activates JNK, reduces the Bcl-2 protein level, promotes mitochondrial translocation of Bax protein, releases cytochrome c into cytoplasm, and finally induces apoptosis. Recently, Hsieh et al. reported that overexpression of REIC/Dkk-3 gene induces apoptosis in different human cancer cells through activation of caspase 3, which is known as a major apoptosis executor downstream of cytochrome c (Hsieh, S.Y. et al., Oncogene 23, 9183-9 (2004)).

At present, it is unclear whether Ad-REIC-induced JNK activation directly or indirectly acts on Bcl-2 and Bax, although Bcl-2 (Yamamoto, K. et al., Mol Cell Biol 19, 8469-78 (1999); and Deng, X. et al., J Biol Chem 276, 23681-8 (2001)), Bcl-XL (Basu, A. et al., FEBS Lett 538, 41-7 (2003)), and Bim (Lei, K. et al., Mol Cell Biol 22, 4929-42 (2002)) have been identified as targets for JNK. It was confirmed that the REIC/Dkk-3 protein was glycosylated and secreted into a culture solution when overexpressed in PC3 cells by Ad-REIC. The amount of β-catenin and the intracellular localization thereof were not affected by Ad-REIC. Thus, it is considered that secreted REIC/Dkk-3 is unlikely to act through the Wnt canonical pathway (data not shown). JNK are thought to be activated through the non-canonical pathway of Wnt signaling or by an intracellular stress sensing system for the overexpressed protein or unknown intracellular factors. In practice, an IL-10 family cytokine (intercellular signal transduction protein) MDA-7/IL-24 (also referred to as MDA7/IL-24) efficiently induces apoptosis in many types of human cancer cells (particularly human prostate cancer cells) even when secretion of the cytokine is blocked (Sauane, M. et al., Cancer Res 64, 2988-93 (2004)). Bax is activated by p53 (Han, J. et al., Genes Dev 10, 461-77 (1996)). However, since PC3 cells are null in p53, apoptosis induction by the REIC gene is independent of the p53 function (Arah, I. N. et al., Anticancer Res 18, 1845-9 (1998)). MDA-7 also selectively induces apoptosis by p53-independent activation of Bax (Su, z. z. et al., Proc Natl Acd Sci U.S.A. 95, 14400-5 (1998)). Recently, Hoang et al. reported that the overexpression of the REIC/Dkk-3 gene did not induce apoptosis in a human osteosarcoma cell line Saos-2 but inhibited invasion and motility of the cells in in vitro experiments (Hoang, B. H. et al., Cancer Res 64, 2734-9 (2004)). REIC/Dkk-3 may exert its anticancer activity at different points.

Since apoptosis induction by REIC/Dkk-3 gene transfection was proved by in vitro studies, the effect of the REIC/Dkk-3 gene upon PC3 cells was examined in vivo (in animal experiments). PC3 cells ($2.5 \times 10^6$) were subcutaneously injected into nude mice. One week later, when the tumor volumes reached 30 to 100 cm$^3$, $2.5 \times 10^8$ pfu of REIC or lacZ was injected intratumorally with the use of adenovectors. The same volume of buffer (PBS) was injected into a control group. Tumor sizes were measured every 3 days during the 27 days following injection. Tumors in the control group and the lacZ group grew gradually during the observation period of 1 month after injection (FIGS. 4A and 4B). In contrast, tumors completely disappeared in 4 out of 5 mice in the REIC group (treatment group). Further, tumors did not completely disappear in 1 out of 5 mice in the REIC group; instead, they shrunk and then remained unchanged over the observation period. The above tumors were resected after the end of the observation period, followed by TUNEL staining (FIG. 4C). No apoptosis was observed in the buffer group or the lacZ group. Meanwhile, in the REIC group, many TUNEL-positive cells were observed 1 month after injection. Selective apoptosis-inducing activity in culture cells and in vivo tumor-inhibitory activity that are exerted by the REIC/Dkk-3 gene strongly indicate that the REIC/Dkk-3 gene can be a target for cancer therapies in addition to p53 and mda-7 (Sauane, M. et al., Cancer Res 64, 2988-93 (2004)). Prostate cancer is one of the most common malignant diseases in Western countries. Various therapeutic measures, including hormone therapies, have been applied to prostate cancer. However, once prostate cancers acquire hormone resistance at later stages, it is difficult to control them by conventional therapies.

This Example indicates that REIC/Dkk-3 can be a new molecular target to counteract highly malignant prostate cancers.

Example 2

Effects of Prostate Cancer Metastasis Inhibition Caused by REIC/Dkk-3 Gene Transfection using Adenovirus Vectors Mouse prostate cancer cells RM-9 ($5.0 \times 10^3$ cells) were injected into prostates of C57BL/6 mice. One week later, $1.2 \times 10^8$ pfu of REIC or lacZ (or PBS) was directly injected intratumorally (mean tumor diameter: 60 mm$^3$) with the use of adenovectors. Tumor growth was significantly inhibited in the REIC/Dkk-3 group (treatment group) compared with the control group and the lacZ group (FIGS. 5 and 6). Tumor diameters were measured every 3 days using a transrectal ultrasonography system previously developed by the present inventors. Tumor volumes (V) were calculated by the following formula: ½×(short diameter)$^2$×(long diameter). FIG. 5 shows ultrasound images and images of mouse intraperitoneal cavities taken with the transrectal ultrasonography system. FIG. 6 shows time-dependent changes in tumor volumes. As shown in FIGS. 5 and 6, stronger tumor inhibition effects were observed in the REIC/Dkk-3 group than were observed in the LacZ group.

The above tumors were resected on days 10 and 16 (3 and 9 days after adenovector injection, respectively), followed by TUNEL staining for detection of apoptotic cells. As a result, a greater number of cells were found to be TUNEL-positive in the REIC/Dkk-3 group compared with the buffer group and the LacZ group (FIGS. 7A and 7B).

Subsequently, in order to analyze metastasis-inhibitory activity of the REIC gene, each group was subjected to laparotomy when prostate cancer volumes reached 750 mm$^3$. Then, intrapelvic lymph nodes were observed. In order to confirm metastasis rates when volumes of primary tumor lesions reached the same level, prostate cancer volumes were measured using transrectal ultrasonography. When tumor diameters reached 750 mm$^3$ in each group, laparotomy was carried out so that intrapelvic lymph nodes were collected. In the control group and the lacZ group, 80% to 85% of mice were found to experience lymph node metastasis. Meanwhile, in the REIC/Dkk-3 group, approximately 40% of mice were found to experience such metastasis (PBS: n=10; Lacz: n=12; and REIC/Dkk-3: n=12) (FIG. 8). Further, the number of lymph node metastasis lesions was counted. The number of lymph node metastasis lesions was 0 to 5 (mean value: 4) in the control group and the lacZ group; however, it was 0 to 2 (mean value: 1) in the REIC/Dkk-3 group (PBS: n=10; Lacz: n=12; and REIC/Dkk-3: n=12) (FIG. 9).

Subsequently, in order to examine the mechanism for metastasis-inhibitory activity of the REIC/Dkk-3 gene, RM-9 was transfected in vitro with REIC/Dkk-3 or lacZ with the use of adenovectors. Then, matrix metalloproteinase (MMP) activity in a culture solution was measured by zymography. The term "zymography" used herein refers to a representative technique for detecting activity of MMP (matrix metalloproteinase) which is a collagen-degrading enzyme that exists in a basal membrane, such activity serving as an index of the invasion/metastasis ability of cancer cells. A culture supernatant or the like is added to gel containing modified collagen (gelatin) that is a substrate for MMP, followed by migration. Then, a reaction solution that activates MMP is added thereto to stain the gel so that bands appear in connection with the presence of enzymatic activity. MMP2 (72 kDa) and MMP9 (92 kDa) are closely associated with basal membrane invasion. RM-9 was transfected with LacZ, human REIC, or the mouse REIC gene at 10 MOI with the use of adenovectors. 6 hours after transfection, the culture solution used was exchanged and the newly exchanged culture solution was collected 42 hours later, followed by zymography. As shown in FIG. 10, significant signal reduction was observed in the REIC/Dkk-3 group compared with the lacZ group. The results indicate that the matrix protease activity was reduced. Thus, it was suggested that such reduction in MMP activity is involved in the metastasis inhibition effects of the REIC/Dkk-3 gene.

Regarding survival curves for orthotopic transplantation models of prostate cancer, survival was significantly extended in the REIC/Dkk-3 group compared with the control group and the LacZ group. As a result of single-dose administration of the REIC/Dkk-3 gene, the improvement was observed in survival rates in addition to effects of localized tumor inhibition and metastasis inhibition (FIG. 11).

The longest survival time extension effect was obtained in the above case compared with the results of gene therapy experiments using the other genes (HSV-tk and IL-12) and the same system (Median survival: control group=22 to 25 days; REIC/Dkk-3 treatment group=42 to 50 days; HSV-tk treatment group=26 days (Prostate Cancer and Prostatic Diseases, 4: 44-55, 2001); and IL-12 treatment group=28 days (Gene Therapy 6: 338-349, 1999)).

Example 3

Relationship Between HSP70 and Apoptosis Induction Caused by Forced Expression of REIC/Dkk-3

It was examined whether tumor selectivity in terms of apoptosis expression caused by Ad-REIC would be associated with HSP70 expression in normal cells and cancer cells.

Normal cells OUMS 24 (human immortalized fibroblast) and prostate cancer cells PC3 were used for comparison. The cells were infected with Ad-REIC at 20 MOI. 24 hours later, an HSP70 inhibitor (heat shock protein inhibitor I, CALBIOCHEM, BIOCHEMICALS) and an HSP70 inducer (Geranyl-Geranyl Acetone) (250 mM each) were separately added to a culture solution. 48 hours later, TUNEL staining was performed to determine influence upon apoptosis. FIGS. 12 and 13 show staining images for OUMS24 and of PC3, respectively. In FIGS. 12 and 13, images on the left side indicate TUNEL-staining results and images on the right side indicate DAPI-staining results. As shown in FIG. 12, among normal cells OUMS24, a large number of TUNEL-positive cells were obtained with the combined use of the Ad-REIC and the HSP70 inhibitor. On the other hand, a small number of TUNEL-positive cells were obtained with the combined use of the Ad-REIC and the HSP inducer. Also, as shown in FIG. 13, among prostate cancer cells PC3, the number of TUNEL-positive cells obtained with the combined use of the Ad-REIC and the HSP70 inhibitor was greater than that obtained with the use of Ad-REIC alone. On the other hand, the number of TUNEL-positive cells obtained with the combined use of the Ad-REIC and the HSP inducer was smaller than that obtained with the use of Ad-REIC alone. That is, apoptosis was induced in normal cells with the use of the HSP70 inhibitor in combination. On the other hand, apoptosis expression was inhibited in cancer cells with the use of the HSP70 inducer in combination. Further, apoptosis induction was promoted with the use of the HSP70 inhibitor in combination.

The above results revealed that apoptosis expression caused by Ad-REIC significantly depends on cell stress responsiveness.

Example 4

PC3 cells and OUMS-24 cells were separately infected with viruses (Ad-LacZ/Ad-REIC) at 20 MOI for 36 hours. Thereafter, the cells were separately placed on media at 45° C. and then the media were placed in an incubator at 45° C. for 6 hours, followed by CBB staining. The cells subjected to heat treatment at 45° C. belong to a heat (+) group (group subjected to hyperthermia following infection). In addition, cells that had not been heat-treated (heat (−) group) were infected with viruses for 42 hours, followed by staining.

Almost all PC3 cells in the group subjected to hyperthermia following infection completely died (FIG. 14). Since cancer cells are generally sensitive to hyperthermia, synergistic effects can be obtained by a therapy involving combined use of cancer hyperthermia, which has been widely examined in medical practice, and the apoptosis-inducing agent of the present invention.

INDUSTRIAL APPLICABILITY

As shown in the Examples, the REIC/Dkk-3 expression level was specifically reduced in highly malignant prostate cancer tissue. In addition, apoptosis was selectively induced in cancer cells by transfecting the REIC/Dkk-3 gene into prostate cancer cells lacking REIC/Dkk-3 expression so as to cause REIC/Dkk-3 expression in such cells. Further, when nude mice into which human prostate cancer cells had been implanted for tumor development were transfected with the REIC/Dkk-3 gene, tumor inhibition was observed. That is, the REIC/Dkk-3 gene of the present invention and an expression product thereof can be used as an apoptosis-inducing agent for prostate cancer cells and a therapeutic agent for prostate cancer, which can cause apoptosis in prostate cancer cells, resulting in prostate cancer inhibition. Furthermore, the REIC/Dkk-3 gene of the present invention and an expression product thereof can be used as agents for inhibiting prostate cancer metastasis, which can inhibit prostate cancer metastasis. Moreover, prostate cancer can be treated more effectively with the combined use of hyperthermia and the REIC/Dkk-3 gene of the present invention and an expression product thereof.

All publications, patents, and patent applications cited herein are incorporated herein by reference in their entirety.

FREE TEXT OF SEQUENCE LISTING

SEQ ID NOS: 3 to 6 (primers)

The invention claimed is:

1. A method for treating localized prostate cancer by inducing apoptosis, which comprises administering intratumorally, as an active ingredient, an adenovirus vector which comprises the following REIC/Dkk-3 DNA consisting of the nucleotide sequence represented by SEQ ID NO: 1 to a patient in need thereof.

2. The method according to claim 1, in which the treatment is done in combination with hyperthermia.

3. A method for inducing apoptosis of prostate cancer cells in localized prostate cancer, which comprises administering intratumorally, as an active ingredient, an adenovirus vector which comprises the following REIC/Dkk-3 DNA consisting of the nucleotide sequence represented by SEQ ID NO: 1 to a patient in need thereof.

4. The method according to claim 3, in which the induction of apoptosis is done in combination with hyperthermia.

5. A method for inhibiting prostate cancer cell growth in localized prostate cancer by inducing apoptosis, which comprises contacting an adenovirus vector which comprises the following REIC/Dkk-3 DNA consisting of the nucleotide sequence represented by SEQ ID NO: 1 intratumorally with prostate cancer cells.

6. The method according to claim 5, in which the inhibition of prostate cancer cell growth is done in combination with hyperthermia.

* * * * *

SEQUENCE LISTING

```
<160> NUMBER OF SEQ ID NOS: 6

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1 atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
            20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
        35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
    50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                85                  90                  95 gag acc aac aca gac acg aag gtt gga aat aat acc atc cat gtg cac     336
Glu Thr Asn Thr Asp Thr Lys Val Gly Asn Asn Thr Ile His Val His
            100                 105                 110 cga gaa att cac aag ata acc aac aac cag gct cga caa atg gtc ttt     384
Arg Glu Ile His Lys Ile Thr Asn Asn Gln Ala Arg Gln Met Val Phe
        115                 120                 125 tca gag aca gtt atc aca tct gtg gga gac gaa gaa ggc aga agg agc     432
Ser Glu Thr Val Ile Thr Ser Val Gly Asp Glu Glu Gly Arg Arg Ser
    130                 135                 140 cac gag tgc atc atc gac gag gac tgt ggg ccc agc atg tac tgc cag     480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg     528
Phe Ala Ser Phe Gln Tyr Thr Cys Gln Pro Cys Arg Gly Gln Arg Met
                165                 170                 175 ctc tgc acc cgg gac agt gag tgc tgt gga gac cag ctg tgt gtc tgg     576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt     624
```

```
            Gly His Cys Thr Lys Met Ala Thr Arg Gly Ser Asn Gly Thr Ile Cys
                    195                 200                 205 gac aac cag agg gac tgc cag ccg ggg ctg tgc tgt gcc ttc cag aga      672
Asp Asn Gln Arg Asp Cys Gln Pro Gly Leu Cys Cys Ala Phe Gln Arg
210                 215                 220 ggc ctg ctg ttc cct gtg tgc ata ccc ctg ccc gtg gag ggc gag ctt      720
Gly Leu Leu Phe Pro Val Cys Ile Pro Leu Pro Val Glu Gly Glu Leu
225                 230                 235                 240 tgc cat gac ccc gcc agc cgg ctt ctg gac ctc atc acc tgg gag cta      768
Cys His Asp Pro Ala Ser Arg Leu Leu Asp Leu Ile Thr Trp Glu Leu
            245                 250                 255 gag cct gat gga gcc ttg gac cga tgc cct tgt gcc agt ggc ctc ctc      816
Glu Pro Asp Gly Ala Leu Asp Arg Cys Pro Cys Ala Ser Gly Leu Leu
            260                 265                 270 tgc cag ccc cac agc cac agc ctg gtg tat gtg tgc aag ccg acc ttc      864
Cys Gln Pro His Ser His Ser Leu Val Tyr Val Cys Lys Pro Thr Phe
            275                 280                 285 gtg ggg agc cgt gac caa gat ggg gag atc ctg ctg ccc aga gag gtc      912
Val Gly Ser Arg Asp Gln Asp Gly Glu Ile Leu Leu Pro Arg Glu Val
290                 295                 300 ccc gat gag tat gaa gtt ggc agc ttc atg gag gag gtg cgc cag gag      960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag     1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag         1053
Pro Ala Ala Ala Ala Ala Leu Leu Gly Gly Glu Glu Ile
            340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Val Glu Asp Thr Gln His Lys
        50                  55                  60

Leu Arg Ser Ala Val Glu Glu Met Glu Ala Glu Ala Ala Lys
65                  70                  75                  80

Ala Ser Ser Glu Val Asn Leu Ala Asn Leu Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175
```

-continued

```
Leu Cys Thr Arg Asp Ser Glu Cys Cys Gly Asp Gln Leu Cys Val Trp
                180                 185                 190
Gly His Cys Thr Lys Met Ala Thr Arg Gly Ser Asn Gly Thr Ile Cys
            195                 200                 205
Asp Asn Gln Arg Asp Cys Gln Pro Gly Leu Cys Cys Ala Phe Gln Arg
210                 215                 220
Gly Leu Leu Phe Pro Val Cys Ile Pro Leu Pro Val Glu Gly Glu Leu
225                 230                 235                 240
Cys His Asp Pro Ala Ser Arg Leu Leu Asp Leu Ile Thr Trp Glu Leu
                245                 250                 255
Glu Pro Asp Gly Ala Leu Asp Arg Cys Pro Cys Ala Ser Gly Leu Leu
            260                 265                 270
Cys Gln Pro His Ser His Ser Leu Val Tyr Val Cys Lys Pro Thr Phe
        275                 280                 285
Val Gly Ser Arg Asp Gln Asp Gly Glu Ile Leu Leu Pro Arg Glu Val
    290                 295                 300
Pro Asp Glu Tyr Glu Val Gly Ser Phe Met Glu Glu Val Arg Gln Glu
305                 310                 315                 320
Leu Glu Asp Leu Glu Arg Ser Leu Thr Glu Glu Met Ala Leu Gly Glu
                325                 330                 335
Pro Ala Ala Ala Ala Ala Leu Leu Gly Gly Glu Glu Ile
            340                 345                 350
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer
<400> SEQUENCE: 3
gtaagttccc ctctggcttg                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer
<400> SEQUENCE: 4
aagcaccaga ctgtgaagcc t                                                21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer
<400> SEQUENCE: 5
gggtgtgaac catgagaagt atga                                             24

<210> SEQ ID NO 6
<211> LENGTH: 20
<212> TYPE: DNA
<213> ORGANISM: Artificial Sequence

```
<220> FEATURE:
<223> OTHER INFORMATION: Description of Artificial Sequence: Primer

<400> SEQUENCE: 6
tgctaagcag ttggtggtgc                                                    20
```